United States Patent
Suetoshi et al.

(10) Patent No.: US 8,246,542 B2
(45) Date of Patent: Aug. 21, 2012

(54) METHOD AND DEVICE OF DIAGNOSING BONE STRENGTH

(75) Inventors: Ryoichi Suetoshi, Nishinomiya (JP); Atsushi Uodome, Nishinomiya (JP); Dorian Cretin, Nishinomiya (JP)

(73) Assignee: Furuno Electric Company, Ltd., Nishinomiya-Shi (JP)

( * ) Notice: Subject to any disclaimer, the term of this patent is extended or adjusted under 35 U.S.C. 154(b) by 508 days.

(21) Appl. No.: 12/509,086

(22) Filed: Jul. 24, 2009

(65) Prior Publication Data
US 2010/0030080 A1 Feb. 4, 2010

(30) Foreign Application Priority Data
Jul. 25, 2008 (JP) .................................. 2008-191694

(51) Int. Cl.
*A61B 8/00* (2006.01)
(52) U.S. Cl. ....................................................... 600/438
(58) Field of Classification Search ................... 600/438
See application file for complete search history.

(56) References Cited

U.S. PATENT DOCUMENTS

| | | | |
|---|---|---|---|
| 5,426,979 A | | 6/1995 | Kantorovich et al. |
| 7,112,173 B1 * | | 9/2006 | Kantorovich et al. ........ 600/449 |
| 2006/0052696 A1 * | | 3/2006 | Shiina et al. .................. 600/437 |

FOREIGN PATENT DOCUMENTS

| | | |
|---|---|---|
| JP | 4-317641 A | 11/1992 |
| JP | 2003-517328 | 5/2003 |
| WO | WO-97/13145 A1 | 4/1997 |
| WO | WO-99/45348 A1 | 9/1999 |
| WO | WO 03/099132 A1 | 12/2003 |
| WO | WO 03/099133 A1 | 12/2003 |
| WO | WO-2008/146513 A1 | 12/2008 |

OTHER PUBLICATIONS

UK Search Report dated Nov. 25, 2009 for corresponding UK Application No. GB0913044.4.

* cited by examiner

*Primary Examiner* — Jonathan Cwern
(74) *Attorney, Agent, or Firm* — Birch, Stewart, Kolasch & Birch, LLP

(57) ABSTRACT

A bone strength diagnostic device includes a wave-transmission module that transmits an ultrasonic wave obliquely to a bone covered with soft tissues; a wave-reception module that receives the ultrasonic wave that exits from the bone to the side of the soft tissues; a shape detection module for detecting the shape of the front surface of the bone; and a speed-of-sound deriving module for deriving the speed of sound of the ultrasonic wave that propagates along the front surface of the bone, based on the received wave signals, and the shape of the front surface of the bone detected using the shape detection module.

10 Claims, 19 Drawing Sheets

METHOD AND DEVICE OF DIAGNOSING BONE STRENGTH

CROSS-REFERENCE TO RELATED APPLICATION(S)

This application claims priority under 35 U.S.C. §119 to Japanese Patent Application No. 2008-191694, which was filed on Jul. 25, 2008, the entire disclosure of which is hereby incorporated by reference.

TECHNICAL FIELD

The present invention relates to a method and device of diagnosing bone strength by transmitting an ultrasonic wave that propagates at the speed of sound along a bone surface.

BACKGROUND

Speed of sound of an ultrasonic wave that propagates inside of a bone can be used for an index of diagnosing bone strength. Conventionally, devices have existed that measures the speed of sound of the ultrasonic wave that propagates along the surface of a long pipe-shaped bone (i.e., long bone) in the longitudinal direction to diagnose bone strength based on the speed of sound.

As devices for measuring the speed of sound of the ultrasonic wave propagating along the bone surface, as shown in FIG. 17A, a device 901 including a transducer 902 for wave transmission and two transducers 903 and 904 for wave reception is well-known. The device 901 measures the speed of sound by the following method assuming that the bone surface is flat, as well as the surface of soft tissues, such as muscles covering the bone, being parallel to each other.

First, the transducer 902 for wave transmission transmits an ultrasonic wave to be incident to the bone surface near a critical angle to generate a surface wave on the bone surface. The surface wave propagates along the bone surface while emitting a leaky surface wave at a predetermined angle (same angle as the critical angle). The leaky surface wave is received by the two transducers 903 and 904 for wave reception. Because the interval between the two transducers 903 and 904 for wave reception is known, the speed of sound of the surface wave can be calculated from a time difference between the times when the transducers 903 and 904 received the leaky surface wave, respectively.

However, the bone surface and the surface of soft tissues may not be parallel to each other and, thus, in that case, the device 901 may produce errors in its calculation results. There are various devices proposed to eliminate the errors (for example, refer to JP2003-517328(A), WO03/099132, and WO03/099133).

As one particular example of such devices, as shown in FIG. 17B, a speed-of-sound measuring device 901' includes two transducers 902 and 905 for wave transmission, and two transducers 903 and 904 for wave reception. The device 901' transmits an ultrasonic wave from the transducer 902 for wave transmission, and receives a leaky surface wave produced due to the transmission with the two transducers 903 and 904 for wave reception. Further, an ultrasonic wave is similarly transmitted from the transducer 905 for wave transmission, and the two transducers 903 and 904 for wave reception receive a leaky surface wave produced due to the transmission.

The speed of sound of the surface wave can be calculated in consideration of inclination of the bone surface by using a time difference between wave-reception timings of the leaky surface wave by the two transducers 903 and 904 for wave reception when the ultrasonic wave is transmitted from the transducer 902 (or 905) for wave transmission, and by using a difference between a propagation time from a wave transmission to a wave reception when the ultrasonic wave is transmitted from the transducer 902 for wave transmission and the leaky surface wave is received by the transducer 903 (or 904) for wave reception and a propagation time from a wave transmission to a wave reception when the ultrasonic wave is transmitted from the transducer 905 for wave transmission and the leaky surface wave is received by the transducer 903 (or 904) for wave reception.

Further, JP2003-517328(A) discloses, in addition to the speed-of-sound measuring device equipped with two transducers for wave transmission and two transducers for wave reception as the device 901' described above, a speed-of-sound measuring device including an arrayed transducer including a plurality of transducers. This device first transmits ultrasonic waves from the arrayed transducer to a bone, and then receives reflected waves from a surface of the bone. The device carries out imaging of a shape of the bone front surface by a known method based on the received wave signals, and then derives the thickness of soft tissues.

The device calculates from the thickness of soft tissues an optimum spaced distance between the transducers for wave transmission and the transducers for wave reception. When the soft tissues are thick, if the interval between the transducers for wave transmission and the transducers for wave reception is too near, leaky surface waves cannot be received. On the other hand, when the soft tissues are thin and the interval between both transducers is too far, only leaky surface waves of small amplitude can be received and, therefore, it may not be desirable. Thus, the optimum distance between the transducers for wave transmission and the transducers for wave reception may vary depending on the thickness of soft tissues.

Next, the device determines two transducers for wave transmission and two transducers for wave reception to be used for a speed-of-sound measurement based on the calculated optimum spaced distance between the transducers for wave transmission and the transducers for wave reception among transducers constituting the arrayed transducer. Then, the device calculates a speed of sound of the surface wave using the four determined transducers.

However, the device 901' or the device disclosed in JP2003-517328(A), WO03/099132, and WO03/099133 calculates a speed of sound based on the propagation course of the ultrasonic wave when the bone surface is flat. Thus, the device can only be applied when the bone surface is flat. Therefore, errors will be greater when a shape of an actual bone surface is curved (for example, when a circumferential speed of sound of a long pipe-shaped bone is measured).

Further, the speed-of-sound measuring device including the arrayed transducer disclosed in JP2003-517328(A) acquires the shape of the bone front surface in an image, using the arrayed transducer. However, this image is only originally used to detect the thickness of soft tissues and determine four transducers to be used for a speed-of-sound measurement among the arrayed transducers based on the thickness and, thus, it is not for calculation of a speed of sound.

SUMMARY

Therefore, the present invention is made to address these situations, and provides a bone strength diagnostic device with a high diagnostic accuracy of bone strength, which can derive the speed of sound of an ultrasonic wave propagating along a bone surface with sufficient accuracy even if the shape of a bone front surface is curved.

According to an aspect of the invention, a bone strength diagnostic device includes a wave-transmission module for deriving a speed of sound that transmits an ultrasonic wave from a wave-transmission transducer for deriving the speed of sound obliquely to a bone covered with soft tissues, a wave-reception module for deriving the speed of sound that receives the ultrasonic wave that exits from the bone to the side of the soft tissues with a plurality of wave-reception transducers for deriving the speed of sound, the ultrasonic wave being received after it is transmitted from the wave-transmission module for deriving the speed of sound and propagates along a front surface of the bone, a shape detection module for detecting the shape of the front surface of the bone, and a speed-of-sound deriving module for deriving the speed of sound of the ultrasonic wave that propagates along the front surface of the bone, based on the received wave signal by the wave-reception module for deriving the speed of sound, and the shape of the front surface of the bone detected by the shape detection module.

An ultrasonic wave is transmitted from the wave-transmission transducer for deriving the speed of sound obliquely to a bone to generate an ultrasonic wave that propagates along the bone front surface. This ultrasonic wave exits from the bone to the side of the soft tissues after propagated along the bone front surface and is received by the plurality of wave-reception transducers for deriving the speed of sound. The speed-of-sound deriving module derives the speed of sound of the ultrasonic wave that propagates along the bone front surface by using the wave signal received by the wave-reception module for deriving the speed of sound and the shape of the bone front surface detected beforehand by the shape detection module, and then diagnoses the bone strength based on the derived speed of sound.

Thus, even if the shape of the bone front surface is curved, by deriving the speed of sound in the bone using the information on the shape of the bone front surface, the speed of sound in the bone can be derived with sufficient accuracy. As a result, the diagnostic accuracy of the bone strength can be improved.

The wave-reception transducer for deriving the speed of sound may include a plurality of wave-reception transducers for deriving the speed of sound. A sound insulating material may be arranged between the wave-transmission module for deriving the speed of sound and the plurality of wave-reception transducers for deriving the speed of sound.

The shape detection module may include a wave-transmission module for shape detection that transmits the ultrasonic wave to the bone, a wave-reception module for shape detection that receives a front-surface reflected wave of the ultrasonic wave from the front surface of the bone, the ultrasonic wave being transmitted from the wave-transmission module for shape detection, and a front surface shape detecting module for detecting the shape of the front surface of the bone using the wave signal received by the wave-reception module for shape detection.

The wave-transmission module for shape detection may include a plurality of wave-transmission transducers for shape detection that transmit the ultrasonic waves simultaneously; and the wave-reception module for shape detection includes a plurality of wave-reception transducers for shape detection that receive the front-surface reflected wave. The front surface shape detecting module may include an incoming direction detecting module for detecting the incoming direction of the front-surface reflected wave to each transducer group using a time difference between times when two wave-reception transducers for shape detection constituting each transducer group receive the front-surface reflected wave, each transducer group including adjacent two wave-reception transducers for shape detection among the plurality of wave-reception transducers for shape detection, a propagation time detecting module for detecting a propagation time of the front-surface reflected wave that reaches each transducer group using the received wave signal of the front-surface reflected wave of at least one wave-reception transducer for shape detection among the two wave-reception transducers for shape detection constituting each transducer group, a front-surface reflection point detecting module for detecting a reflection point of the ultrasonic wave on the front surface of the bone based on the incoming direction and the propagation time of the front-surface reflected wave detected for each transducer group by the incoming direction detecting module and the propagation time detecting module, respectively, and a shape deriving module for deriving the shape of the front surface of the bone using the plurality of reflection points on the front surface of the bone, the reflection points being detected for the plurality of transducer groups having different transducers by the front-surface reflection point detecting module.

The wave-transmission transducer for shape detection may function as the wave-reception transducer for shape detection as well.

The wave-reception transducer for deriving the speed of sound may function as the wave-reception transducer for shape detection as well.

The shape detection module may perform detection of a shape of a back surface of the bone in addition to the detection of the shape of the front surface of the bone.

The wave-reception module for shape detection may perform wave reception of the back-surface reflected wave from the back surface of the bone that reaches the plurality of wave-reception transducers for shape detection after the front-surface reflected wave in addition to performing the wave reception of the front-surface reflected wave. The incoming direction detecting module may perform detection of an incoming direction of the back-surface reflected wave to each transducer group using a time difference between times when the two wave-reception transducers for shape detection constituting each transducer group receives the back-surface reflected wave in addition to performing detection of the incoming direction of the front-surface reflected wave. The propagation time detecting module may perform detection of the propagation time of the back-surface reflected wave that reaches each transducer group using the received wave signal of the back-surface reflected wave of at least one wave-reception transducer for shape detection among the two wave-reception transducers for shape detection constituting each transducer group in addition to performing the detection of the propagation time of the front-surface reflected wave that reaches each transducer group. The shape detecting module may include a back-surface reflection point detecting module for detecting a reflection point of the ultrasonic wave on the back surface of the bone based on the incoming direction and the propagation time of the back-surface reflected wave detected for each transducer group by the incoming direction detecting module and the propagation time detecting module, and the shape of the front surface of the bone derived by the shape deriving module. The shape deriving module may derive the shape of the back surface of the bone with the back-surface reflection point detecting module using the plurality of reflection points on the back surface of the bone that are detected for the plurality of transducer groups having different transducers.

The bone strength diagnostic device may further comprises a damping coefficient detecting module for detecting a damping coefficient of the ultrasonic wave received by the wave-reception module for deriving the speed of sound based on the transmitted wave signal of the wave-transmission module for deriving the speed of sound and the received wave signal of the wave-reception module for deriving the speed of sound.

According to another aspect of the invention, a method of diagnosing bone strength includes detecting a shape of a front surface of a bone covered with soft tissues, transmitting an ultrasonic wave obliquely to the bone, receiving the ultrasonic wave that exits from the bone to the side of the soft tissues at a plurality of locations after it is transmitted and propagates along the front surface of the bone, and deriving a speed of sound of the ultrasonic wave that propagates along the front surface of the bone based on the received wave signal and the detected shape of the front surface of the bone.

An ultrasonic wave is transmitted obliquely to a bone to generate an ultrasonic wave that propagates along the bone front surface. This ultrasonic wave exits from the bone to the side of the soft tissues after propagated along the bone front surface and is received by the plurality of locations. The speed of sound of the ultrasonic wave that propagates along the bone front surface is derived using the received wave signal and the detected shape of the bone front surface to diagnose the bone strength based on the derived speed of sound.

Thus, even if the shape of the bone front surface is curved, by deriving the speed of sound in the bone using the information on the shape of the bone front surface, the speed of sound in the bone can be derived with sufficient accuracy. As a result, the diagnostic accuracy of the bone strength can be improved.

BRIEF DESCRIPTION OF THE DRAWINGS

The present disclosure is illustrated by way of example and not by way of limitation in the figures of the accompanying drawings, in which the like reference numerals indicate like elements and in which:

FIG. 15A shows an arrayed transducer of Modified Embodiment 7, FIG. 15B shows an arrayed transducer of Modified Embodiment 8, and FIG. 15C shows an ultrasonic transceiver having an arrayed transducer of Modified Embodiment 9 added with a change-over circuit;

FIG. 16A shows an ultrasonic transceiver of Modified Embodiment 12, FIG. 16B shows an ultrasonic transceiver of Modified Embodiment 13, and FIG. 16C shows an ultrasonic transceiver of Modified Embodiment 14.

DETAILED DESCRIPTION

Hereinafter, embodiments of the invention is explained referring to the appended drawings.

Embodiment 1

A bone strength diagnostic device 1 of an embodiment of the invention derives a speed of sound of an ultrasonic wave propagating along a surface of a bone to diagnose the strength of the bone based on the speed of sound.

The bone strength diagnostic device 1 diagnoses a bone inside a body such as, but not limited to, a cortical bone of long-pipe shape, such as a tibia, for example. Typically, a bone is configured with a cortical bone part and a cancellous bone part, in the shape of lattice-shaped spicules, existing in the inner side of cortical bone.

Figure 1:
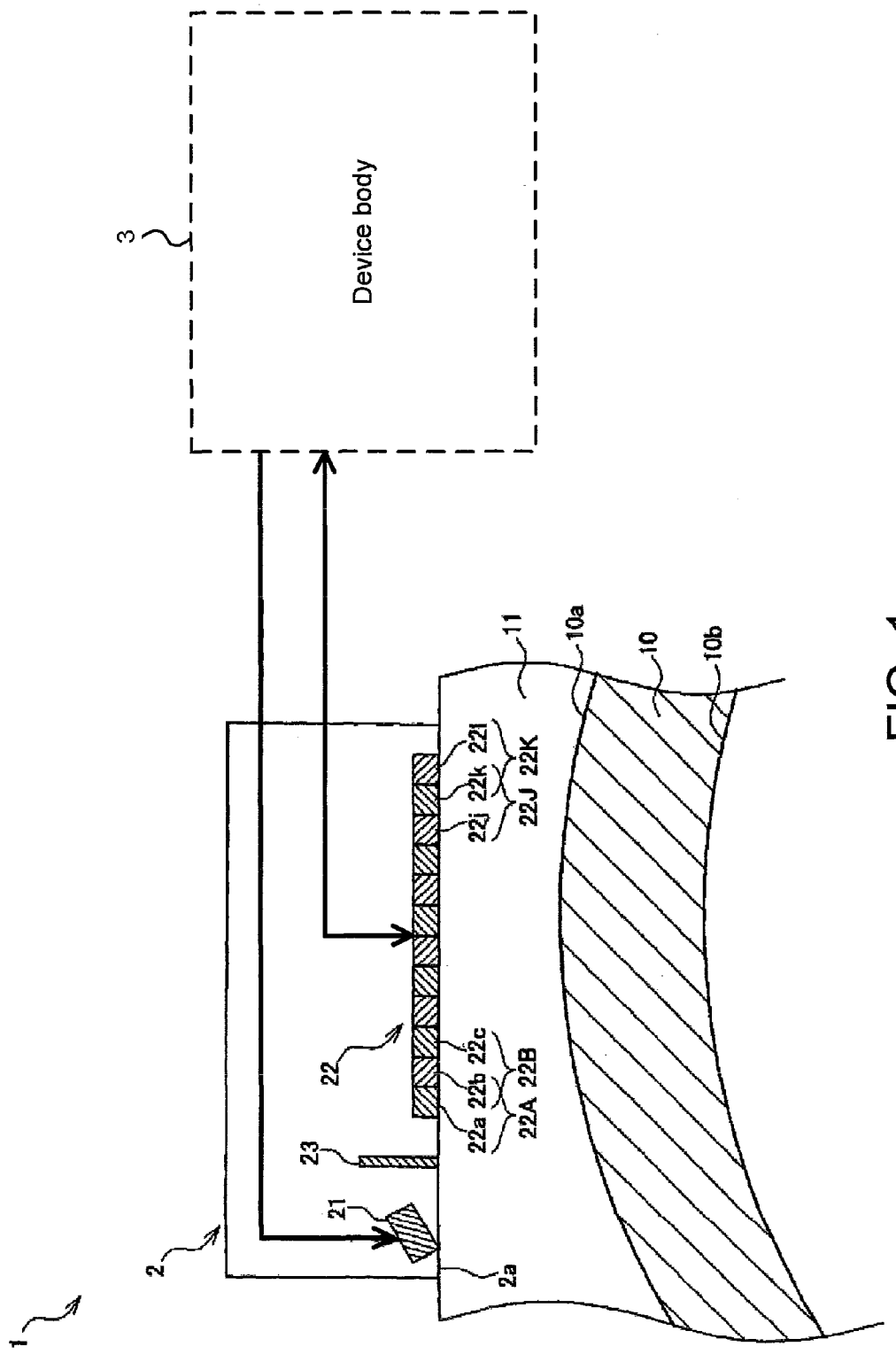
FIGS. 1 and 1B are a schematic diagram showing a configuration of a bone strength diagnostic device according to an embodiment of the present invention.

As shown in FIG. 1, a surface 10a of a cortical bone 10 (hereinafter, simply referred to as a "bone" in this embodiment) is covered with soft tissues 11, such as muscles and fat. FIG. 1 shows a cross-section perpendicular to the longitudinal direction of the bone 10 (i.e., transverse cross-section), and a shape of the bone front surface 10a is formed in a loosely curved surface which is convex toward the side of the soft tissues 11. In this embodiment, although illustration is omitted, the surface of the longitudinal cross-section of the bone 10 may be substantially flat and may be inclined with respect to the surface of the soft tissues 11.

The bone strength diagnostic device 1 of this embodiment derives the speed of sound of an ultrasonic wave propagating along the bone front surface 10a in the circumferential direction (hereinafter, referred to as a "circumferential speed of sound") and the speed of sound of an ultrasonic wave propagating along the bone front surface 10a in the longitudinal direction (hereinafter, referred to as a "longitudinal speed of sound"), and then diagnoses the strength of the bone using the speeds of sound of these two directions.

Figure 1B:
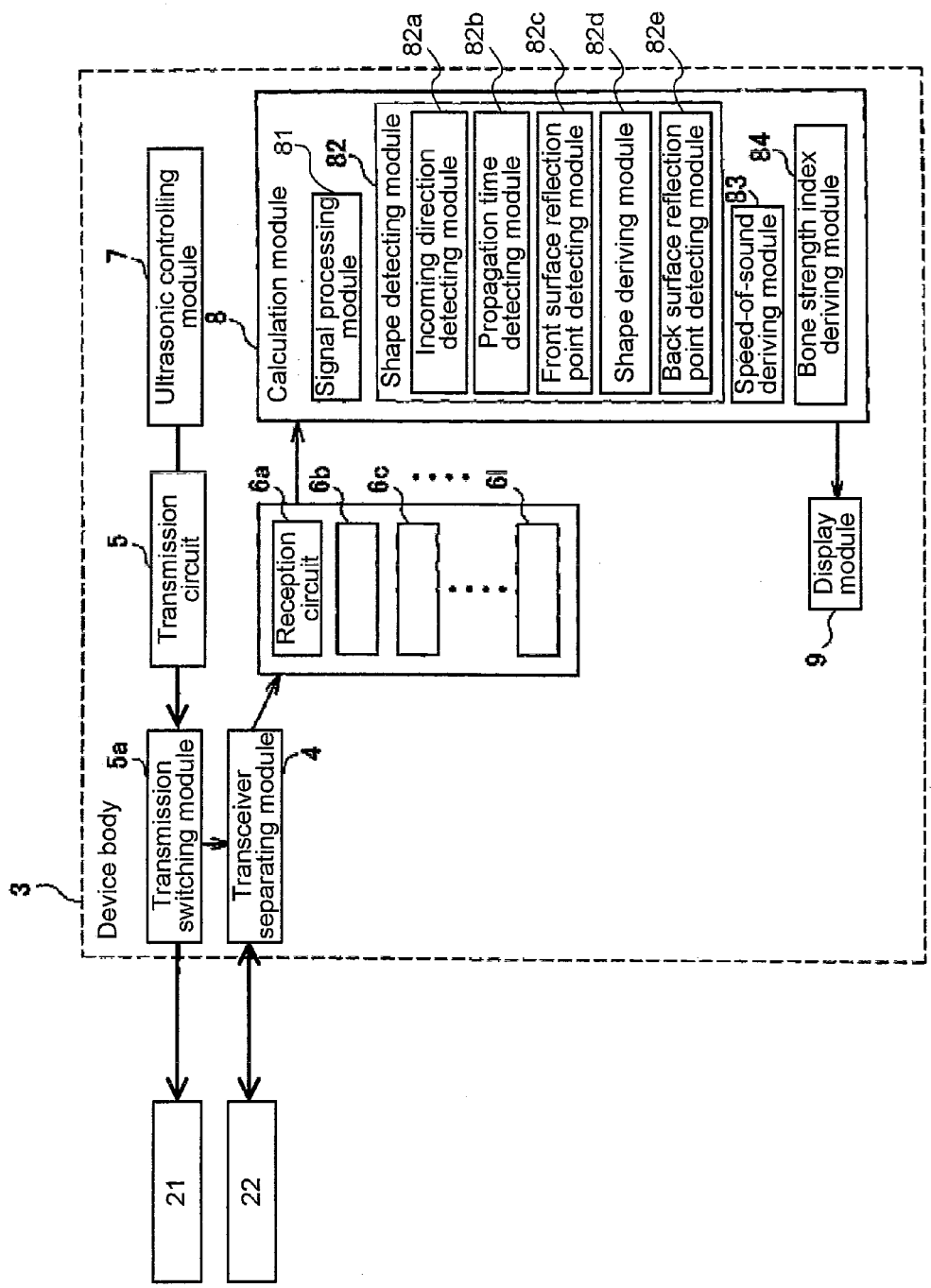

As shown in FIG. 1, the bone strength diagnostic device 1 of this embodiment includes an ultrasonic transceiver 2 and a device body 3. The device body 3 includes, as shown in FIG. 1B, a transceiver separating module 4, a transmission circuit 5, a transmission switching module 5a, a plurality of reception circuits 6a-6l, an ultrasonic controlling module 7, a calculation module 8, and a display module 9.

The ultrasonic transceiver 2 transmits and receives an ultrasonic wave, and is contacted with a surface of the soft tissues 11. The surface of the transducer 2 contacted with the surface of the soft tissues 11 is called herein a "contacting face 2a." The ultrasonic transceiver 2 includes a transducer 21 dedicated to wave transmission, an arrayed transducer 22 having a plurality of transducers 22a-22l (twelve transducers in this embodiment) arranged in a single row, and a sound insulating material 23. The transducer used herein is such that it oscillates when an electric signal is applied to generate an ultrasonic wave from its surface (oscillating surface), and on the other hand, it generates an electric signal when it receives an ultrasonic wave on its surface to be oscillated.

The transducer 21 dedicated to wave transmission, the sound insulating material 23, and the arrayed transducer 22 are aligned in the arrayed direction of the arrayed transducer 22. When measuring the circumferential speed of sound, as shown in FIG. 1, the bone ultrasonic wave transceiver 2 is contacted with the soft tissues 11 so that the arrayed direction of the arrayed transducer 22 is oriented substantially in the circumferential direction of the bone 10. On the other hand, when measuring the longitudinal speed of sound, the ultrasonic transceiver 2 is contacted the soft tissues 11 so that the arrayed direction of the arrayed transducer 22 is oriented substantially in the longitudinal direction of the bone 10.

The transducer 21 dedicated to wave transmission is provided so that its surface (oscillating surface) inclines to the contacting face 2a. As the transducer 21 dedicated to wave transmission, what transmits an ultrasonic wave with a wide directivity may be used (in other words, what has a wide angle range of emitting an ultrasonic wave). The smaller the area of the oscillating surface, the wider the directivity becomes. That is, because sensitivity for the ultrasonic wave and the directivity have a trade-off relation, the installation angle of the transducer 21 dedicated to wave transmission and the dimension of the oscillating surface are designed suitable for the object to be measured.

The twelve transducers 22a-22l that constitute the arrayed transducer 22 are arranged so that their surfaces (oscillating surface) are parallel to the contacting face 2a. Note that, although the number of transducers that constitute the arrayed transducer 22 is twelve in this embodiment, it may be any arbitrary number other than twelve. A horizontal length of the arrayed transducer 22 in the case of FIG. 1 may be 24 mm, for example.

In this embodiment, the sound insulating material 23 is formed in a plate shape and is arranged between the transducer 21 dedicated to wave transmission and the arrayed transducer 22. The material of the sound insulating material 23 may be a material having a sound absorbing function, such as cork, a synthetic rubber, a porous material (for example, a foamed resin material), etc. The sound insulating material 23 prevents the ultrasonic wave transmitted from the transducer 21 dedicated to wave transmission from propagating inside of the ultrasonic transceiver 2 to directly reach the arrayed transducer 22. In other words, it can prevent that an ultrasonic wave unnecessary for deriving a speed of sound in the bone is received by the arrayed transducer 22.

Note that a coupling material (not illustrated) intervenes between the contacting face 2a and the surface of the soft tissues 11. The coupling material prevents a gap from being produced between the contacting face 2a and the surface of the soft tissues 11. In addition, the coupling material adjusts acoustic impedances of the transducers 22a-22l and the soft tissues 11 to suppress the ultrasonic wave transmitted from the transducer 21 dedicated to wave transmission or the arrayed transducer 22, reflecting on the surface of the soft tissues 11.

The transducer 21 dedicated to wave transmission is connected to the transmission circuit 5 via the transmission switching module 5a. The plurality of transducers 22a-22l are connected to the transmission circuit 5 via the transceiver separating module 4 and the transmission switching module 5a. The transmission circuit 5 generates an electric pulse signal to be transmitted to the transmission switching module. Note that a chirp signal may be used instead of the electric pulse signal. The center frequency of the electric pulse oscillation may be approximately 1 to 10 MHz, for example.

The transmission switching module 5a transmits the electric pulse signal transmitted from the transmission circuit 5 to any of the transducers 21 dedicated to wave transmission and the arrayed transducer 22. The transmission switching module 5a changes over the transducers to select one that transmits an ultrasonic wave.

The twelve transducers 22a-22l that constitute the arrayed transducer 22 are connected to twelve reception circuits 6a-6l via the transceiver separating module 4, respectively. The reception circuits 6a-6l perform a process, such as an amplifying process, a filtering process, a digital conversion process of the electric signal transmitted from the transducers 22a-22l, respectively (of the received wave signal), and then transmit it to the calculation module 8.

The transceiver separating module 4 prevents the transmitted wave signal sent to the arrayed transducer 22 from the transmission circuit 5 (electric pulse signal) from flowing into the reception circuits 6a-6l directly, and prevents the received wave signal sent to the reception circuits 6a-6l from the arrayed transducer 22 from flowing into the transmission circuit 5.

The ultrasonic controlling module 7 is connected with the transmission circuit 5 and transmits a signal for transmitting ultrasonic waves from the twelve transducers 22a-22l to the transmission circuit 5.

Note that the wave-transmission transducer for deriving the speed of sound in the claims corresponds to the transducer 21 dedicated to wave transmission. Further, the plurality of wave-reception transducers for deriving the speed of sound, the plurality of wave-transmission transducers for reflected waves, and the plurality of wave-reception transducers for reflected waves in the claims correspond to the twelve transducers 22a-22l that constitute the arrayed transducer 22. Therefore, in this embodiment, the wave-reception transducer for deriving the speed of sound serves as the wave-reception transducer for shape detection as well. Thus, the number of transducers that receive the ultrasonic wave can be reduced. Further, in this embodiment, because the wave-transmission transducer for shape detection serves as the wave-reception transducer for shape detection as well, the number of transducers used for the detection of the bone shape can also be reduced.

Further, in this embodiment, the wave-transmission module for deriving the speed of sound in the claims includes the transducer 21 dedicated to wave transmission and the transmission circuit 5. The wave-transmission module for shape detection in the claims includes the arrayed transducer 22 and the transmission circuit 5. The wave-reception module for deriving the speed of sound and the wave-reception module for shape detection in the claims include the arrayed transducer 22 and the twelve reception circuits 6a-6l.

Hereinafter, an operation of the ultrasonic transceiver 2 will be explained.

When Ultrasonic Wave is Transmitted from Arrayed Transducer 22

When the arrayed transducer 22 is determined by the transmission switching module 5a to be a transducer that transmits an ultrasonic wave, an electric pulse signal is sent from the transmission circuit 5 to the arrayed transducer 22. The transducers 22a-22l that constitute the arrayed transducer 22 transmit the ultrasonic waves of the same phase to the bone 10 simultaneously (incident wave). As shown in FIG. 2A, the incident waves transmitted from the arrayed transducer 22 propagate inside of the soft tissues 11 as a plane wave. This plane wave travels in a direction perpendicular to the contacting face 2a.

Figure 2B:
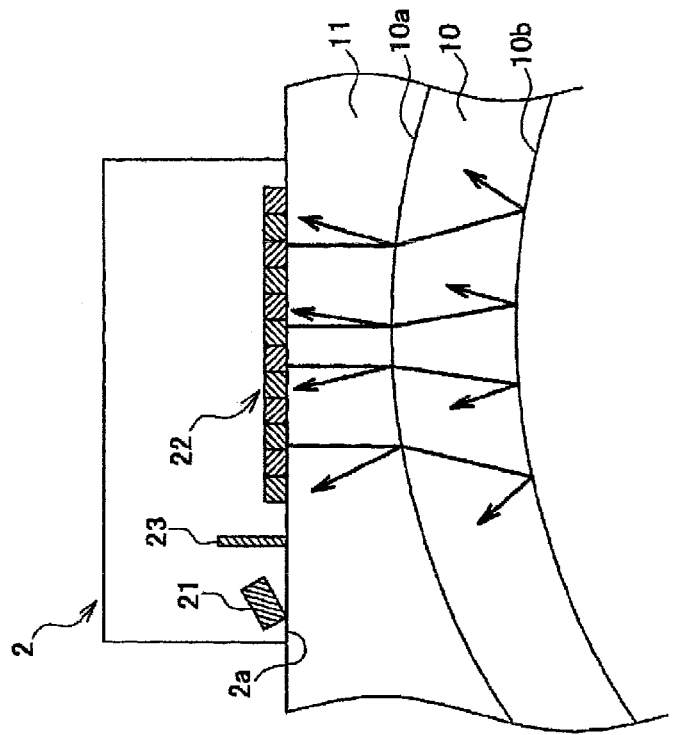
FIG. 2B is a schematic view for illustrating propagation courses of the ultrasonic wave transmitted from the arrayed transducer.
Figure 2A:
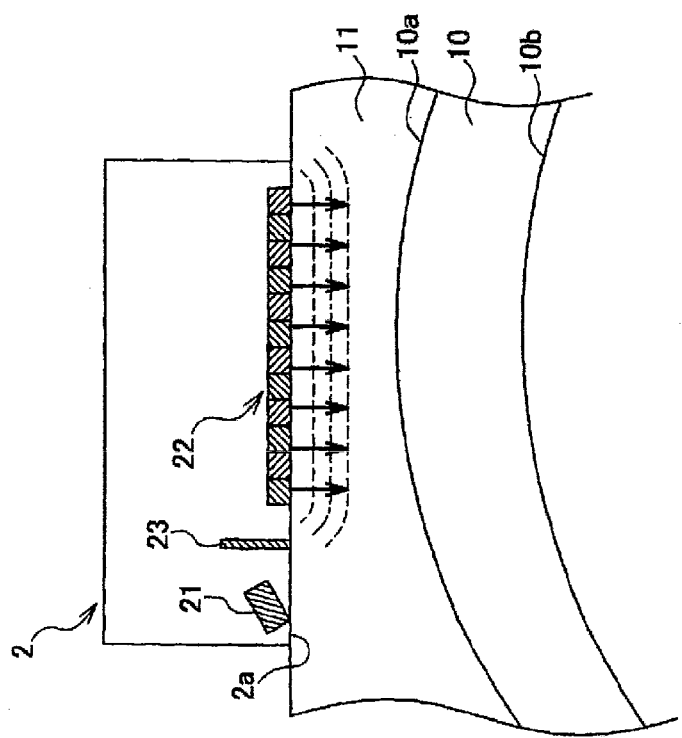
FIG. 2A is a schematic view for illustrating an ultrasonic wave transmitted from an arrayed transducer.

As shown in FIG. 2B, a part of the incident wave is reflected on the bone front surface 10a. A front-surface reflected wave produced by this is received by the transducers 22a-22l. On the other hand, another part of the incident wave that propagates inside of the bone 10 without reflecting on the bone front surface 10a is reflected on the back surface 10b of the bone 10. The back-surface reflected wave produced by this is received by the transducers 22a-22l after the front-surface reflected wave. Therefore, the front-surface reflected wave or the back-surface reflected wave received by each of the transducers 22a-22l may not be determined from which transducer transmitted.

Preferably, a spatial relationship from the arrayed transducer 22 to the bone front surface 10a may be a short-distance field such that the plane wave transmitted from the arrayed transducer 22 propagates to the bone front surface 10a without being spread. Thus, an accuracy of detecting the shape of the bone front surface 10a can be improved. Preferably, the distance from the arrayed transducer 22 to the bone back surface 10b may also be close.

When the transducers 22a-22l receive the front-surface reflected wave or the back-surface reflected wave, they converts the acoustic wave into an electric signal, and then transmit the electric signal (received wave signal) to the reception circuits 6a-6l via the transceiver separating module 4, respectively. Thus, the wave reception of the front-surface reflected wave and the back-surface reflected wave is performed independently by the transducers 22a-22l.

Figure 3:
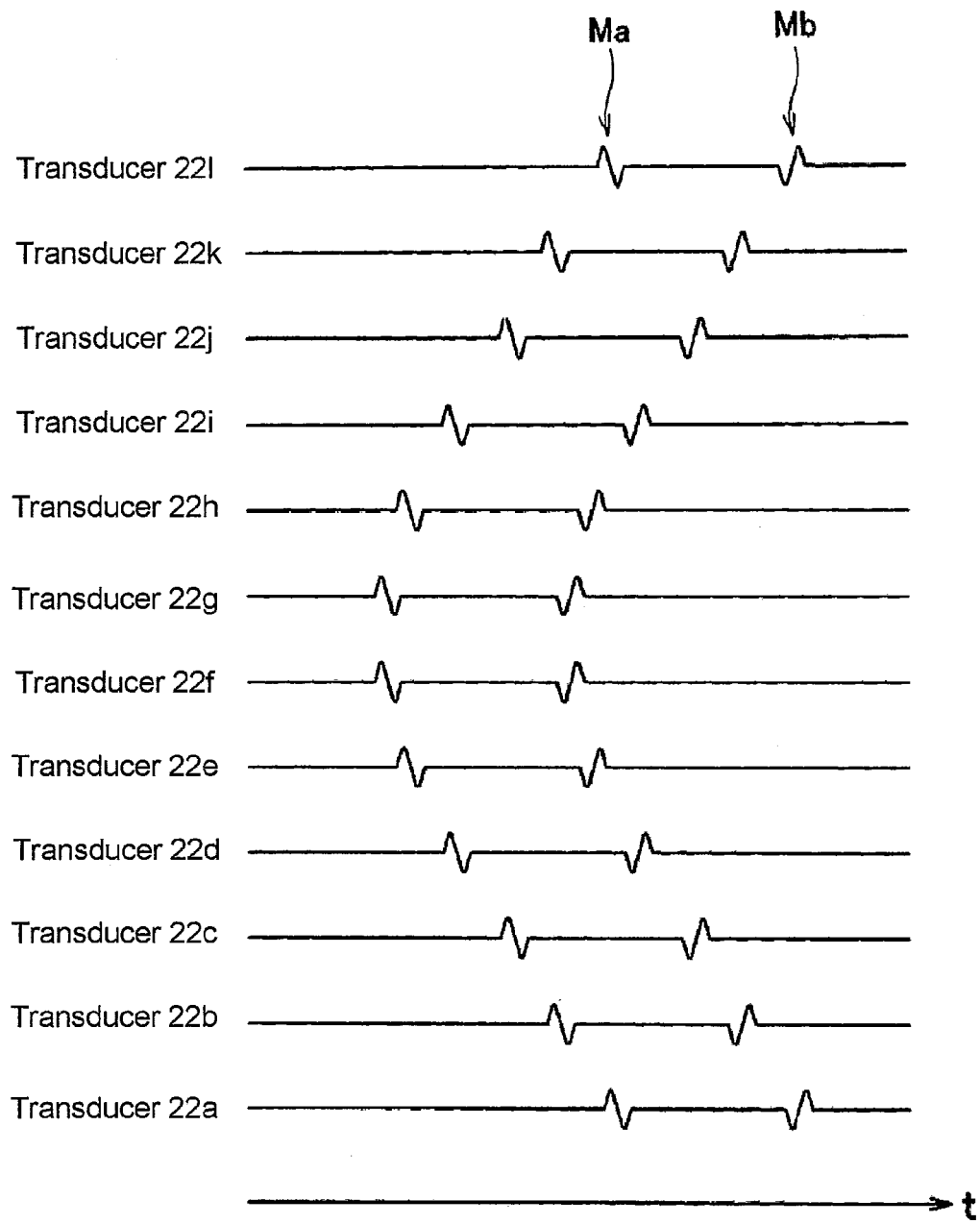
FIG. 3 is a timing chart showing received wave signals of the arrayed transducer.

FIG. 3 shows an example of the received wave signals by the transducers 22a-22l. The horizontal axis of FIG. 3 represents a time after the transmission of the incident wave. A wavefront Ma in FIG. 3 represents the front-surface reflected wave, and a wavefront Mb represents the back-surface reflected wave. The back-surface reflected wave may be inverted in phase because it reflects at the change of acoustic impedance from a coarse part (cancellous bone) to a dense part (cortical bone).

Figure 4:
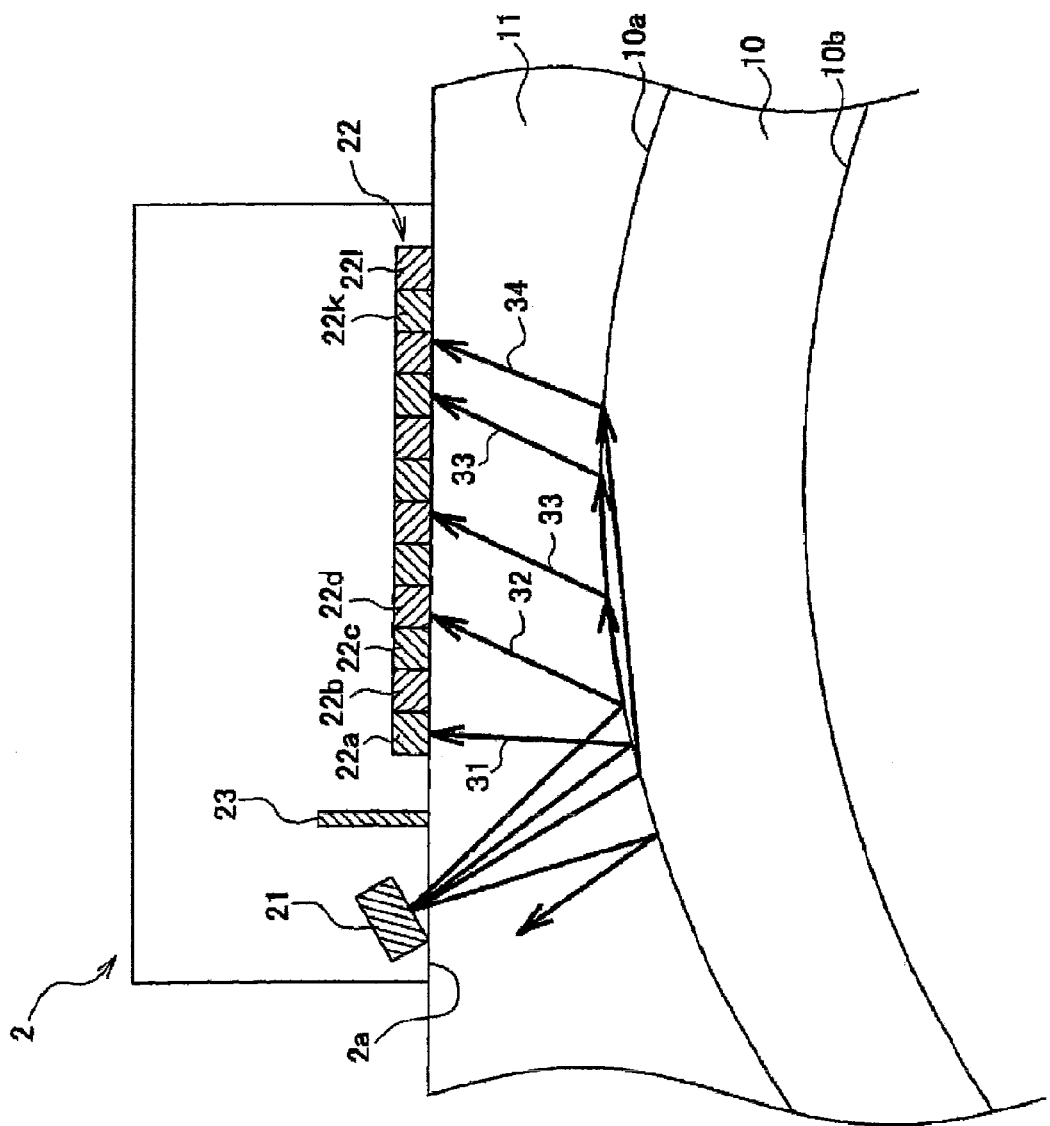
FIG. 4 is a schematic view for illustrating propagation courses of the ultrasonic wave transmitted from a transducer dedicated to wave transmission.

When Ultrasonic Wave is Transmitted from Transducer 21 Dedicated to Wave Transmission When the transmission switching module 5a determines the transducer 21 dedicated to wave transmission to be a transducer that transmits an ultrasonic wave, an electric pulse signal is sent from the transmission circuit 5 to the transducer 21 dedicated to wave transmission, and the transducer 21 dedicated to wave transmission then transmits an ultrasonic wave to the bone 10. As shown in FIG. 4, from the transducer 21 dedicated to wave transmission, an ultrasonic wave with a wide directivity (incident wave) is transmitted. The incident wave that propagates inside of the soft tissues 11 in a direction inclined to the contacting face 2a.

The ultrasonic wave transmitted from the transducer 21 dedicated to wave transmission is received by the arrayed transducer 22 via a plurality of propagation routes. Like the case where an ultrasonic wave is transmitted from the arrayed transducer 22, the transducers 22a-22l transmits the received wave signal to the reception circuits 6a-6l, respectively, when they receive the ultrasonic waves.

The following three types exist for the propagation routes of the ultrasonic wave that is transmitted from the transducer 21 dedicated to wave transmission and reaches the arrayed transducer 22. One route is a propagation route where an ultrasonic wave propagates along the surface of the soft tissues 11 and then reaches the arrayed transducer 22 directly. Another route is a propagation route where an ultrasonic wave reflects on the bone front surface 10a and then reaches the arrayed transducer 22 (propagation route including the reflected wave 31 or the reflected wave 32 in FIG. 4). Still another route is the propagation route where the ultrasonic wave propagates along the bone front surface 10a and after that, exits to the side of the soft tissues 11 from the bone 10 and then reaches the arrayed transducer 22. Two types among these three types of the propagation routes are explained below.

When a part of the incident wave is incident on the bone front surface 10a near at the critical angle, a surface wave will occur on the bone front surface 10a. This surface wave propagates along the bone front surface 10a, while emitting a leaky surface wave in a predetermined direction toward the soft tissues 11 (direction near at the critical angle with respect to the bone front surface 10a). This leaky surface wave is received by the arrayed transducer 22. An ultrasonic wave 33 in FIG. 4 is shown as an example of the leaky surface wave. The critical angle is determined based on the speed of sound in the soft tissues 11 and the speed of sound in the bone 10. Because the transducer 21 dedicated to wave transmission is used as a transducer with a wide directivity, even if the inclination of the bone front surface 10a varies depending on examinees, it is possible to make the ultrasonic wave be incident on the bone front surface 10a near at the critical angle.

When the part of the incident wave is incident on the bone front surface 10a at an angle smaller than the critical angle, it is refracted by the bone front surface 10a and then propagates in the vicinity of the bone front surface 10a of the bone 10, and after that, it is again refracted by the interface 10a of the bone 10 and the soft tissues 11. This refracted wave (hereinafter, referred to as a "bone front-surface refracted wave") is received by the arrayed transducer 22. An ultrasonic wave 34 in FIG. 4 is shown as an example of the bone front-surface refracted wave. The bone front-surface refracted wave is generated only when the shape of the bone front surface 10a is not flat.

Both the bone front-surface refracted wave and the leaky surface wave may be received by a single transducer that constitutes the arrayed transducer 22. The bone front-surface refracted wave may be received before or after the leaky surface wave is received.

When a bone width (a length of the bone 10 in the horizontal direction of FIG. 1) is small, the leaky surface wave may not reach a position sufficiently distant from the transducer 21 dedicated to wave transmission. That is, the smaller the bone width becomes, the shorter the range within which the leaky surface wave can be received will be. Although it may depend on the inclination of the bone front surface 10a relative to the contacting face 2a, the distance between a transducer among the transducers capable of receiving the leaky surface wave which is the closest to the transducer 21 dedicated to wave transmission and the transducer 21 dedicated to wave transmission will be longer as the thickness of the soft tissues 11 is thicker. In this embodiment, because the leaky surface wave is received by the plurality of transducers 22a-22l, even if the bone width or the thickness of the soft tissues 11 varies for individual examinees, it is possible to certainly receive the leaky surface wave by at least one of the plurality of transducers among the plurality of transducers 22a-22l.

As described above, the leaky surface wave can only be received at a position with some distance from the transducer 21 dedicated to wave transmission. On the other hand, the reflected wave from the bone surface 10a can be received even at a position close to the transducer 21 dedicated to wave transmission. For example, in the case of FIG. 4, the leaky surface wave will be received by the transducer 22d and the transducers on the right of the transducer 22d, but the reflected wave from the bone surface 10a will be received by the transducer 22a and the transducers on the right of the transducer 22a. Thus, the transducers on the side of the transducer 21 dedicated to wave transmission in the arrayed transducer 22 may receive only the reflected wave, and may not receive the leaky surface wave.

When both the leaky surface wave and the reflected wave from the bone front surface 10a are received by one transducer constituting the arrayed transducer 22, the leaky surface wave is received before the reflected wave. This is because the speed of sound in the bone 10 is faster than the speed of sound in the soft tissues 11.

An ultrasonic wave that propagates along the surface of the soft tissues 11 and reaches the arrayed transducer 22 directly (hereinafter, referred to as a "direct wave") reaches a transducer near the transducer 21 dedicated to wave transmission before the leaky surface wave. However, the ultrasonic wave may reach after the leaky surface wave a transducer apart from the transducer 21 dedicated to wave transmission. Note that, due to the existence of the sound insulating material 23, the amplitude of the direct wave is designed to be very small compared with the amplitude of the leaky surface wave or the reflected wave.

Referring back to FIG. 1B, the calculation module 8 includes a CPU, a RAM, and a ROM (these are not illustrated), and also includes a signal processing module 81, a shape detecting module 82, a speed-of-sound deriving module 83, and a bone strength index deriving module 84.

The signal processing module 81 includes a memory module and a signal processing circuit (these are not illustrated). The signal processing module 81 receives the received wave signals transmitted from the reception circuits 6a-6l and stores in the memory module the received wave signals within a predetermined period of time from the wave transmission of the ultrasonic wave. The signal processing module 81 then detects a peak value of the received wave signals with the signal processing circuit, and transmits it to the shape detecting module 82 and the speed-of-sound deriving module 83.

The shape detecting module 82 detects shapes of the bone front surface 10a and the bone back surface 10b by using the received wave signals of the front-surface reflected wave and the back-surface reflected wave of the arrayed transducer 22 when the ultrasonic wave is transmitted from the arrayed transducer 22. The shape detecting module 82 includes an incoming direction detecting module 82a, a propagation time detecting module 82b, a front-surface reflection point detecting module 82c, a shape deriving module 82d, and a back-surface reflection point detecting module 82e.

The incoming direction detecting module 82a determines eleven transducer groups 22A-22K (refer to FIG. 1), each group having adjacent two transducers among the twelve transducers 22a-22l, and detects incoming directions of the front-surface reflected waves and the back-surface reflected waves that reach each of the transducer groups 22A-22K.

The propagation time detecting module 82b detects a propagation time of the front-surface reflected wave and a propagation time of the back-surface reflected wave that reach each of the transducer groups 22A-22K.

The front-surface reflection point detecting module 82c detects eleven reflection points on the bone front surface 10a (front-surface reflection points) based on the incoming directions and the propagation times of the front-surface reflected waves which reached the eleven transducer groups 22A-22K and which are detected by the incoming direction detecting module 82a and the propagation time detecting module 82b, respectively.

The shape deriving module 82d derives a shape of the bone front surface 10a using the eleven front-surface reflection points detected by the front-surface reflection point detecting module 82c. Further, the shape deriving module 82d derives a shape of the bone back surface 10b using the eleven back-surface reflection points detected by the back-surface reflection point detecting module 82e described later, and also derives a thickness of the bone 10 (cortical bone) based on the shapes of the bone front surface 10a and the bone back surface 10b.

The back-surface reflection point detecting module 82e detects eleven reflection points on the bone back surface 10b (back-surface reflection points) based on the incoming directions and the propagation times of the back-surface reflected waves which reach the eleven transducer groups 22A-22K, respectively and which are detected by the incoming direction detecting module 82a and the propagation time detecting module 82b.

The speed-of-sound deriving module 83 derives the speed of sound of the ultrasonic wave that propagates along the bone front surface 10a based on the received wave signal of the leaky surface wave or the bone front-surface refracted wave of the arrayed transducer 22 and the shape of the bone front surface 10a derived by the shape deriving module 82d when the ultrasonic wave is transmitted from the transducer 21 dedicated to wave transmission.

The bone strength index deriving module 84 derives an index related to a strength of the bone using the speed of sound in the two directions of the bone 10 derived by the speed-of-sound deriving module 83 and the thickness of the bone 10 derived by the shape deriving module 82d.

The display module 9 is connected with the calculation module 8 to display the shapes of the bone front surface 10a and the back surface 10b derived by the shape deriving module 82d, and a diagnostic index of the bone strength derived by the bone strength index deriving module 84.

Figure 5:
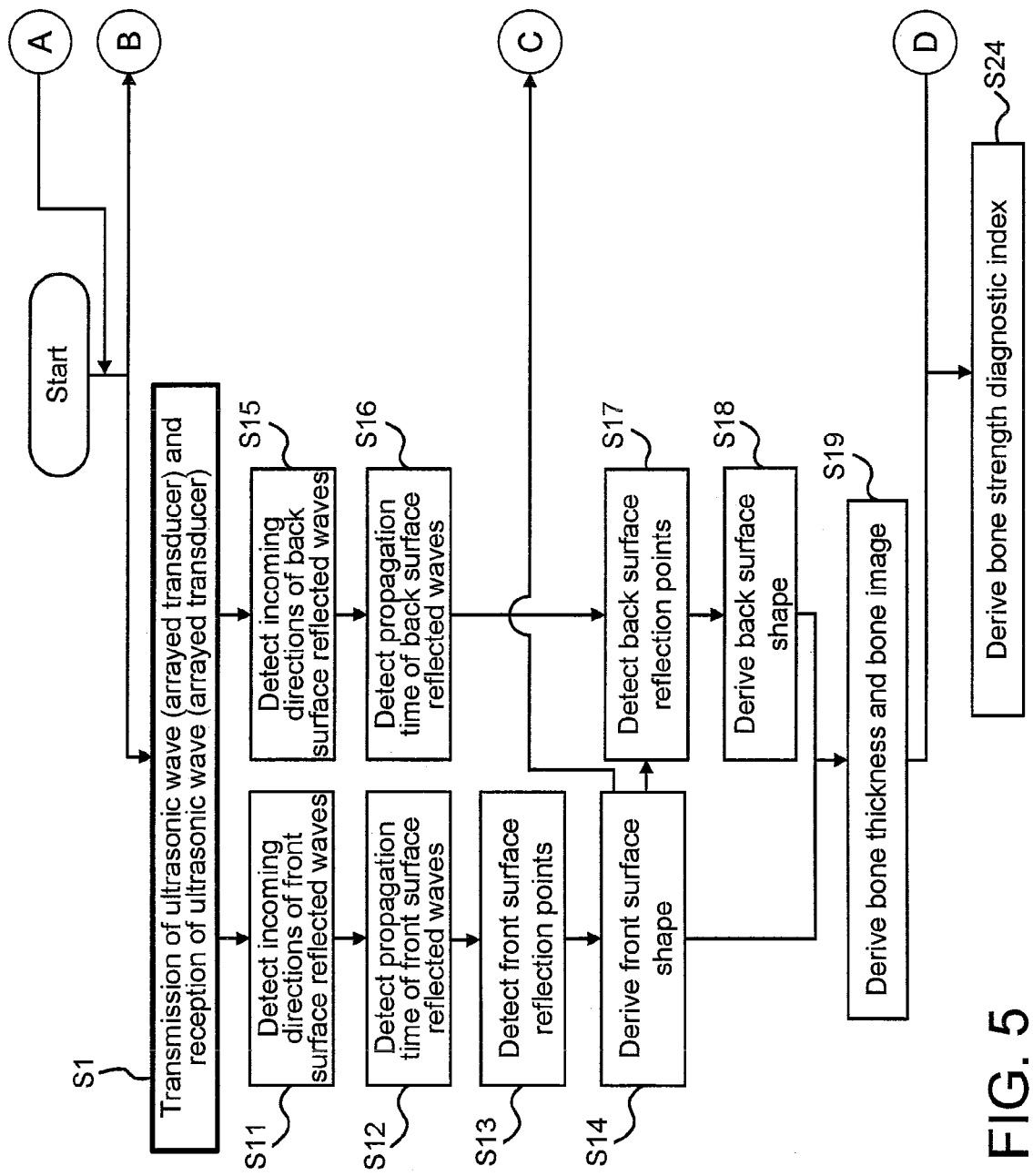
FIGS. 5 and 5B are a flowchart showing an operation of bone strength diagnostic device.
Figure 5B:
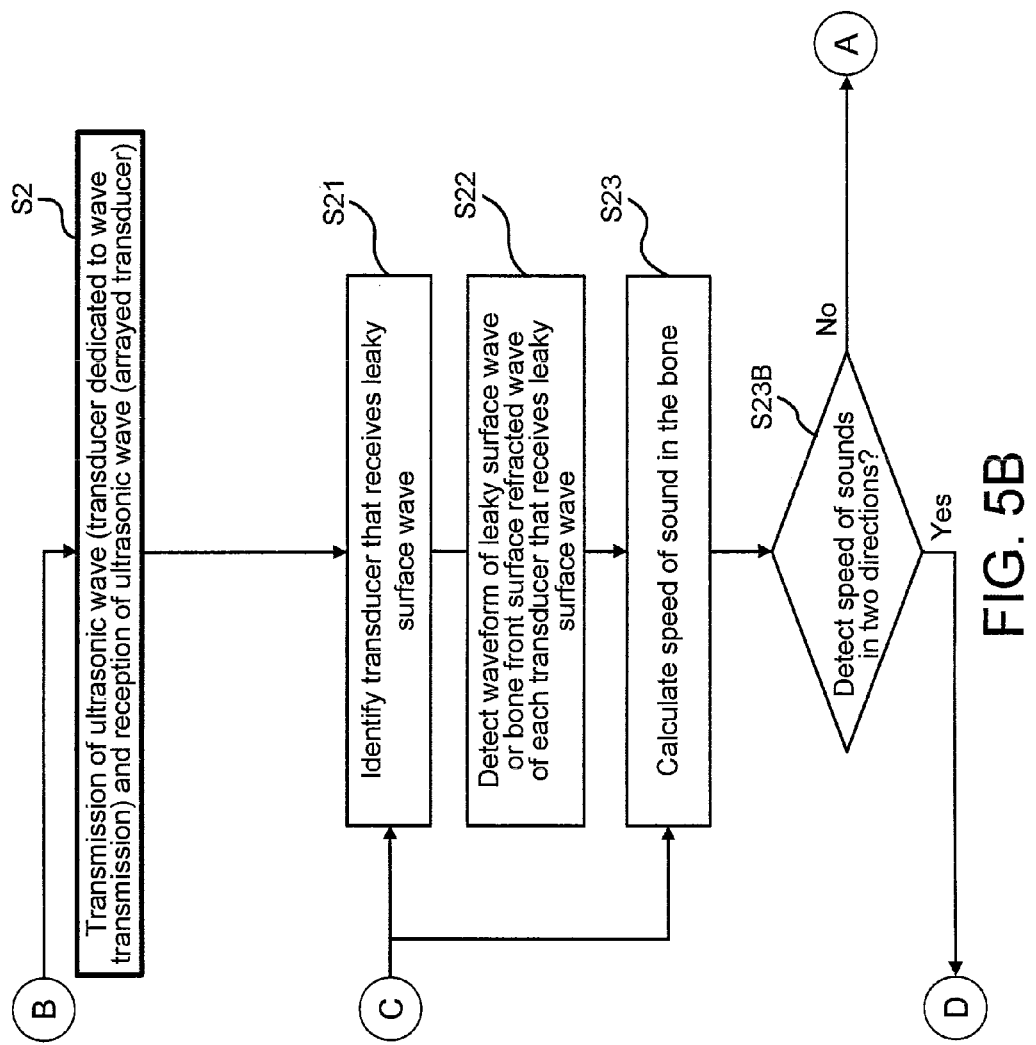

Next, an operation of the bone strength diagnostic device 1 is explained particularly focusing on an operation of the calculation module 8. FIGS. 5 and 5B are a flowchart showing the operation of the bone strength diagnostic device 1.

As shown in FIGS. 5 and 5B, the arrayed transducer 22 performs wave transmission and wave reception of ultrasonic waves (S1), and then, the transducer 21 dedicated to wave transmission transmits an ultrasonic wave without moving the position of the ultrasonic transceiver 2 and the ultrasonic wave is received by the arrayed transducer 22 (S2).

Shape Detection Step

The shape detecting module 82 derives a shape of the bone front surface 10a using the received wave signals of the arrayed transducer 22 when the ultrasonic wave is transmitted from the arrayed transducer 22. First, the incoming direction detecting module 82a detects respective incoming directions of the front-surface reflected waves for the eleven transducer groups 22A-22K (S11).

Two incoming directions of the front-surface reflected waves for two adjacent transducers constituting each transducer group (for example, the transducers 22a and 22b) are close to each other. Therefore, the incoming direction detecting module 82a detects one incoming angle per one transducer group considering that the two incoming directions are the same. Hereinafter, a method of detecting the incoming angle with respect to the transducer group 22A is explained in detail.

Figure 6B:
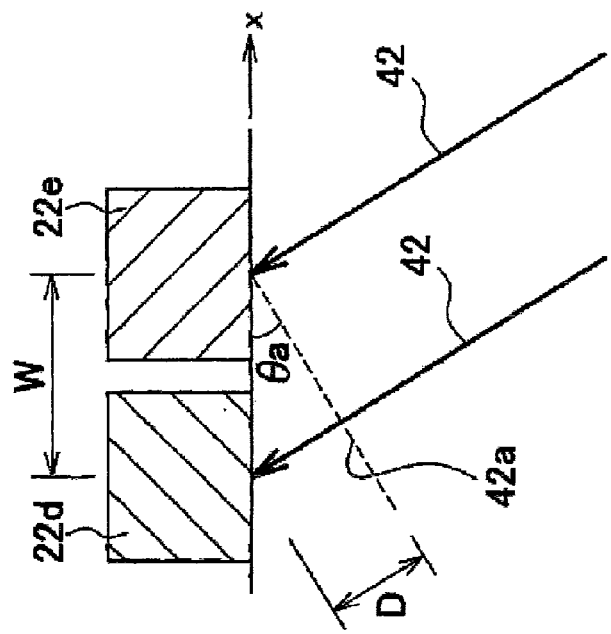
FIG. 6B is a schematic view for illustrating a method of detecting an incoming direction.
Figure 6A:
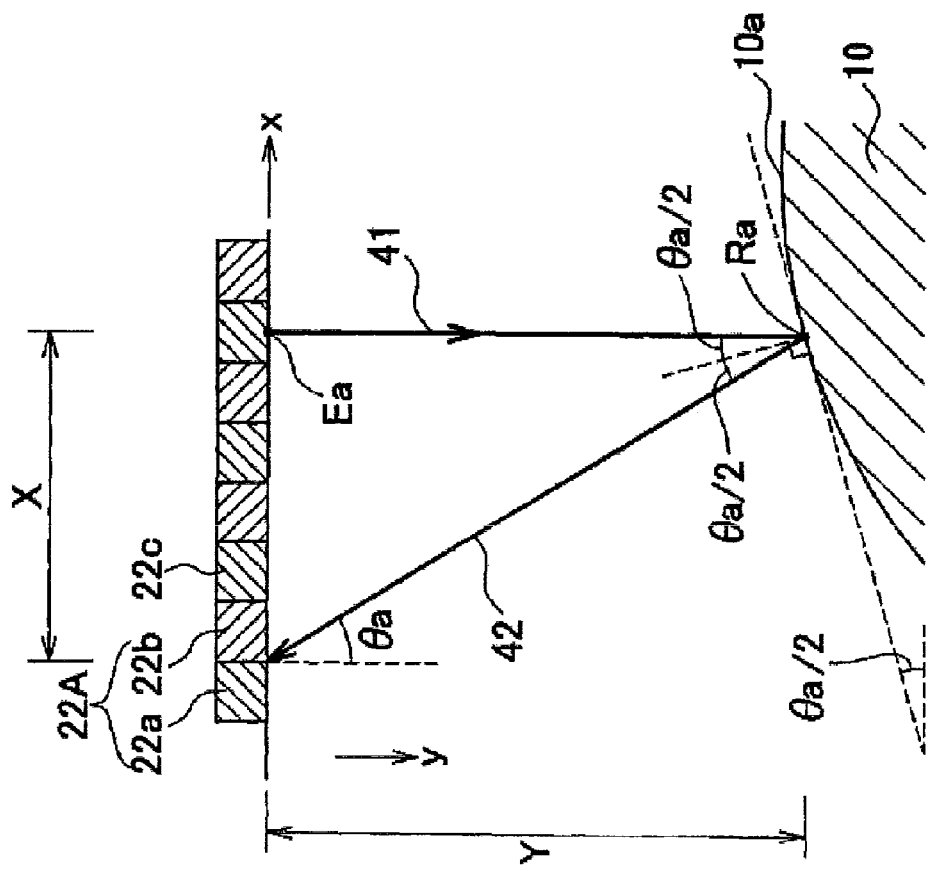
FIG. 6A is a schematic view for illustrating a method of detecting a front-surface reflection point.

As shown in FIG. 6A, it is assumed that the incoming angle of the front-surface reflected wave 42 that reaches the transducer group 22A is set to θa. In this case, as shown in FIG. 6B, because the incoming angles of the front-surface reflected waves that reaches the two transducers 22a and 22b is θa, a wave face 42a of the front-surface reflected waves 42 is inclined at the angle θa with respect to the arranged direction of the arrayed transducer 22 (the x-axis direction in FIG. 6B). Therefore, one front-surface reflected wave 42 reaches the transducer 22b after another front-surface reflected wave 42 reached the transducer 22a, which further travels by a distance D. That is, the transducer 22b receives the front-surface reflected wave 42 after the transducer 22a. Here, the time difference between the times at which the two transducers 22a and 22b receive the front-surface reflected wave 42 is set to Δt.

The following method may be used for deriving Δt based on the received wave signals of the transducers 22a and 22b. For example, the time difference between maximum peaks of the received wave signals of the two transducers 22a and 22b may also be used. Alternatively, so called the "zero-crossing method" may be used in which the time difference between intersecting point of rising parts of the maximum peaks of the received wave signals of the two transducers 22a and 22b with the line of zero amplitude may also be used. Alternatively, a correlation processing with a waveform stored in advance in the calculation module 8 may also be performed to derive the time difference Δt. Alternatively, a phase difference between the received wave signals of the two transducers 22a and 22b may also be obtained by the quadrature detection method or the like to derive the time difference Δt with the obtained phase difference and the frequency of the incident wave. Note that this method can be used only when the phase difference between the received wave signals of the two transducers 22a and 22b is 180 degrees or less.

If the speed of sound in the soft tissues 11 is assumed to be Vs, the difference D of the propagation course can be calculated by D=Vs*Δt. As shown in FIG. 6B, when an interval between the two transducers 22a and 22b is assumed to be W, the difference D of the propagation course can be expressed by D=W*sin θa. Therefore, the incoming angle θa can be calculated by θa=arcsin (Vs*Δt/W). Although the measured value may be used for the speed of sound Vs in the soft tissues 11, an assumed value may also be used.

As described above, although the method of detecting the incoming angle θa of the front-surface reflected wave 42 with respect to the transducer group 22A is explained, the incoming angles θa for other ten transducer groups 22B-22K may also be detected with a similar procedure.

When detecting the incoming direction, the incoming angle may be directly detected from the phase difference between the received wave signals of two transducers constituting a transducer group. The term used herein "using the time difference between times at which the wave-reception transducers receive a front-surface reflected wave, respectively" of the incoming direction detecting module of this embodiment also includes using a phase difference.

Next, the propagation time detecting module 82b detects propagation times Ta after the ultrasonic wave is transmitted by the arrayed transducer 22 until the front-surface reflected waves reach the transducer groups 22A-22K using the received wave signals of the two transducers 22a and 22b (S12). Although an average value of times after the ultrasonic wave is transmitted by the arrayed transducer 22 until the front-surface reflected waves 42 reach the transducers 22a and 22b may be used for the propagation times Ta, values other than the average value may also be used. When the average value is used, errors in the detected shape of the bone front surface 10a can be reduced.

Next, the front-surface reflection point detecting module 82c detects the front-surface reflection points on the bone front surface 10a using the incoming angles θa and the propagation times Ta of the front-surface reflected waves which reach the transducer groups 22A-22K, respectively (S13). Hereinafter, the method of detecting the position of front-surface reflection points on the bone front surface 10a is explained using the incoming angles θa with respect to the transducer group 22A.

As shown in FIG. 6A, when the incoming angle of the front-surface reflected wave 42 with respect to the transducer group 22A is θa, this front-surface reflected wave 42 is a reflection of the incidence wave 41, which is transmitted from a point Ea on the surface of the transducers 22a-22l and travels in the y-axis direction in FIG. 6A, to a point (front-surface reflection point) Ra on the bone front surface 10a inclined at θa/2 from the x-axis direction.

Here, as shown in FIG. 6A, the distance from the transducer group 22A in the x-axis direction to the surface reflection point Ra is set to X, and the distance from the transducer group 22A in the y-axis direction to the surface reflection point Ra is set to Y.

Because the propagating direction of the incident wave 41 is the y-axis direction, the distance from the point Ea to the surface reflection point Ra is Y. In addition, because the distance from the surface reflection point Ra to the transducer group 22A can be expressed by Y/cos θa, the propagation distance La after the incident wave 41 is transmitted from the point Ea until the front-surface reflected wave 42 reaches the transducer group 22A can be expressed by La=Y+Y/cos θa. In addition, the propagation distance La can be calculated by La=Vs*Ta from the propagation time Ta and the speed of sound Vs in the soft tissues. Therefore, Y can be calculated by Y=Vs*Ta*cos θa/(1+cos θa), and X can be calculated by X=Vs*Ta*sin θa/(1+cos θa). Thus, the position of the surface reflection point Ra can be detected.

The propagating direction of the ultrasonic wave (plane wave) transmitted from the arrayed transducer 22 is known beforehand. Therefore, even if it is not determined from which transducer the front-surface reflected wave 42 received in the transducer group 22A is transmitted, the position of the surface reflection point Ra can be detected by using the incoming angle θa and the propagation time Ta which are detected.

As described above, the method of detecting the position of one front-surface reflection point Ra is explained using the incoming angle θa and the propagation time Ta of the front-surface reflected wave that reaches the transducer group 22A. However, the positions of the surface reflection points Ra can be detected with a similar procedure for other ten transducer groups 22B-22K.

In the method described above, the average value of the propagation times of the front-surface reflected waves received by the two transducers constituting a transducer group is set to be the propagation time Ta. However, the propagation time of the front-surface reflected wave received by one of the two transducers may be set to the propagation time Ta as it is. In this case, it may be desirable to use transducers of each transducer group that receive wave signals of the front-surface reflected waves in the same spatial relationship. For example, when using the received wave signal of the transducer 22b in the transducer group 22A, the received wave signal of the transducer 22c is used in the transducer group 22B (in this case, the right transducer of each group is used).

Further, two reflection points may be detected for one transducer group using propagation times and the incoming angle θa of the front-surface reflected waves received by two transducers constituting the transducer group. The term used herein "the propagation time of the front-surface reflected wave that reaches each transducer group" of the propagation time detecting module includes a case where the propagation times of the front-surface reflected waves received by the two transducers are used as "the propagation time of the front-surface reflected wave that reaches each transducer group" as they are.

Figure 7:
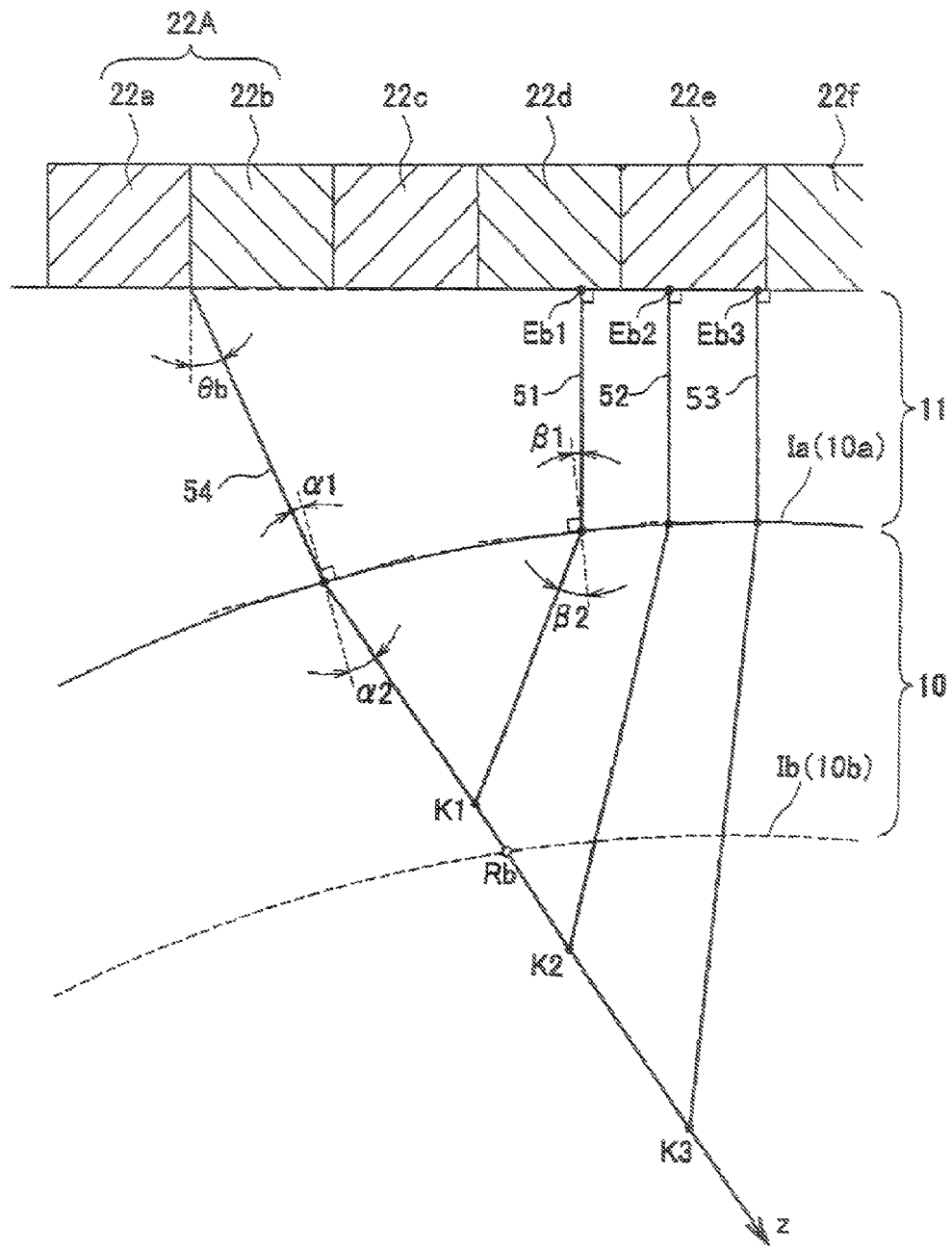
FIG. 7 is a schematic view for illustrating a method of detecting a back-surface reflection point.

The shape deriving module 82d derives a bone front surface line Ia in the x-y plane as shown in FIG. 7 connecting the eleven surface reflection points Ra detected by the front-surface reflection point detecting module 82c with a straight line or a curve (S14). The bone front surface line Ia is displayed on the display module 9 together with a bone back surface line Ib derived later. A size (outer diameter) of the bone 10 can be estimated by using the bone front surface line Ia. Note that the term used herein "deriving the shape of the bone front surface using a plurality of reflection points" by the shape deriving module is not limited to connecting a plurality of reflection points to derive the front surface line, but may include simply acquiring the spatial relationship of the plurality of reflection points.

Next, the shape of the bone back surface 10b is derived. First, the incoming direction detecting module 82a and the propagation time detecting module 82b detect an incoming direction θb and a propagation time Tb0 of a back-surface reflected wave, respectively, that reaches each of the transducer groups 22A-22K by a similar method as the case of the front-surface reflected wave 42 (S15, S16). Note that, because there is a time difference as shown in FIG. 3 between the received wave signal of the front-surface reflected wave and the received wave signal of the back-surface reflected wave for each transducer, they are easily distinguishable.

Next, the back-surface reflection point detecting module 82e detects the position of the back-surface reflection point on the bone back surface 10b using the incoming direction θb and the propagation time Tb0 of the back-surface reflected wave that reaches each of the transducer groups 22A-22K and the bone front surface line Ia derived by the shape deriving module 82d (S17). Hereinafter, the case where back-surface reflection points on the bone back surface 10b is detected for the transducer group 22A using the incoming angle θb and the propagation time Tb0 is explained.

As shown in FIG. 7, an angle of refraction α1 in the bone front surface 10a of the back-surface reflected wave 54 is calculated from the incoming angle θb of the back-surface reflected wave 54 that reaches the transducer group 22A and the bone front surface line Ia.

If the assumed value of the speed of sound in the bone 10 is Vb', and the angle of incidence of the back-surface reflected wave 54 to the soft tissues 11 is α2, the relation of sin α1/sin α2=Vs/Vb' can be satisfied by Snell's law. From this equation, the angle of incidence α2 is calculated, and the propagating direction (z-axis in FIG. 7) in the bone 10 of the back-surface reflected wave 54 is derived.

Further, the angle of incidence β1 of the incident wave 51 to the bone front surface 10a is calculated from the propagating direction (y-axis direction) of the incident wave 51 transmitted from the point Eb1 on the surface of the transducers 22a-22l to the bone front surface 10a, and the bone front surface line Ia.

If an angle of refraction of the incident wave 51 in the bone front surface 10a is set to β2, a relation of sin β1/sin β2=Vs/Vb' can be satisfied by Snell's law. From this equation, the angle of refraction β2 is calculated, and as shown in FIG. 7, the propagating direction of the incident wave 51 in the bone 10 is derived. An intersecting point of the propagating direction of the incident wave 51 in the bone 10 and the propagating direction (z-axis) of the back-surface reflected wave 54 in the bone 10 is set to K1.

Assuming that the intersecting point K1 is a reflection point on the bone back surface 10b (back-surface reflection point), the incident wave 51 transmitted from the point Eb1 would have reflected on the point K1 in the bone back surface 10b, and will have reached the transducer group 22A. In this assumed propagation route, a predicted value of the propagation time from wave transmission to wave reception is set to Tb1. Tb1 can be calculated from the propagation route of the ultrasonic wave from the point Eb1 to the transducer group 22A, using the speed of sound Vs in the soft tissues 11 and the assumed value Vb' of the speed of sound in the bone 10.

In addition, for the incident waves 52 and 53 transmitted from the points Eb2 and Eb3 on the surface of the transducers 22a-22l, the intersecting points K2 and K3 of the propagating direction in the bone 10 and the z-axis are also detected, respectively, similar to the incident wave 51. Further, the predicted values Tb2 and Tb3 of the propagation time from the wave transmission to the wave reception are calculated when the intersecting points K2 and K3 are set to the back-surface reflection point, respectively.

Figure 8:
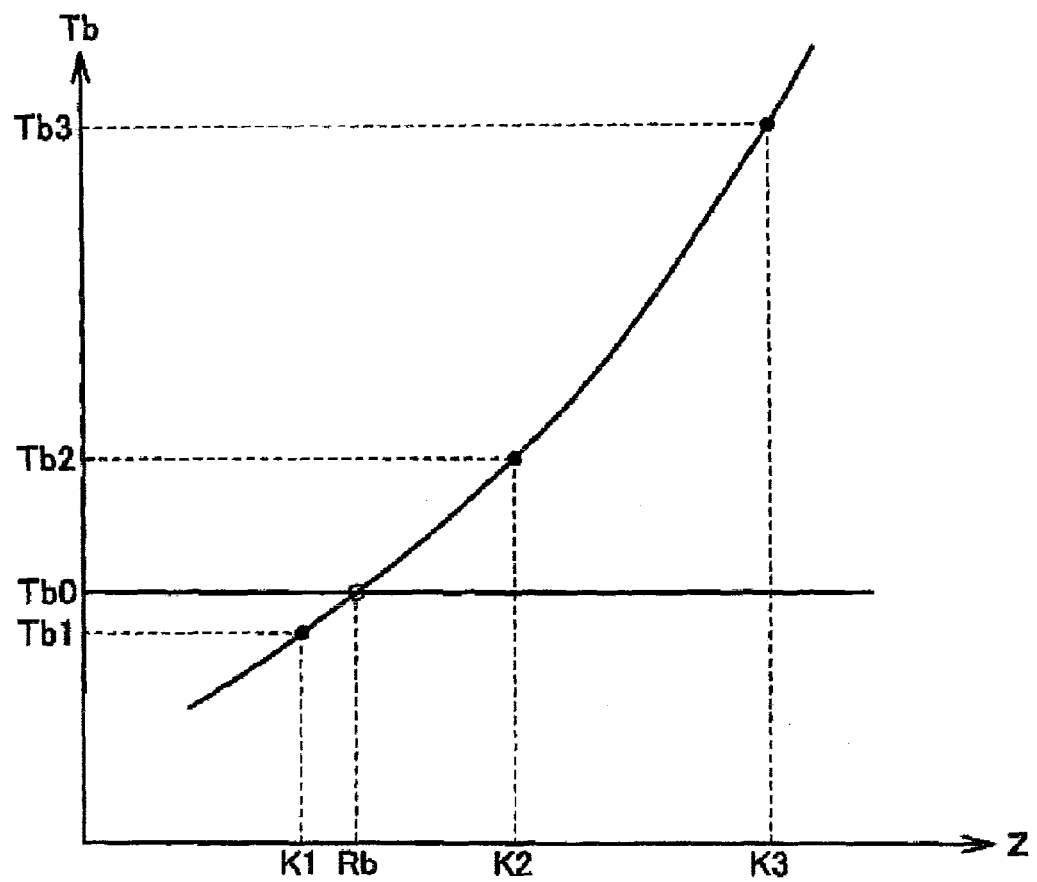
FIG. 8 is a graph to be used for the detection of the back-surface reflection point, showing a relation between a propagation time and a position of the back-surface reflection point.

FIG. 8 shows a graph showing a relation between a position of the back-surface reflection points on the z-axis and the propagation time Tb from wave transmission of the incident wave until the back-surface reflected wave reaches the transducer group 22A. A curve in FIG. 8 connects three points acquired from the predicted values Tb1, Tb2, and Tb3 of the propagation time when assuming the intersecting point K1, K2, and K3 to be the back-surface reflection points. A position of the back-surface reflection points Rb can be detected from an intersecting point of the curve and a line of Tb=Tb0 (actual measurement of the propagation time).

When any of the predicted values Tb1, Tb2, and Tb3 of the calculated propagation time is almost equal to the actual measurement Tb0 of the propagation time, the back-surface reflection points Rb can be detected without using the graph as shown in FIG. 8.

As described above, only the method of detecting one back-surface reflection point Rb using the incoming angle θb and the propagation time Tb0 of the back-surface reflected wave that reaches the transducer group 22A is explained. However, a similar procedure can be applied to the detection at a position of the back-surface reflection points Rb for each of the remaining ten transducer groups 22B-22K.

The shape deriving module 82d derives a bone back surface line Ib in the x-y plane connecting the detected eleven back-surface reflection points Rb with a straight line or a curve, as shown in FIG. 7 with a dashed line (S18).

The derived bone back surface line Ib is displayed on the display module 9 together with the bone front surface line Ia. Thus, an image of the bone can be obtained. Further, the shape deriving module 82d derives the thickness of the bone 10 using the bone front surface line Ia and the bone back surface line Ib (S19).

As explained above, the bone strength diagnostic device 1 of this embodiment simultaneously transmits the ultrasonic waves of the same phase from the plurality of transducers 22a-22l constituting the arrayed transducer 22, and then derives the shape of the bone front surface 10a and the back surface 10b using the reflected waves. Typically, when ultrasonic waves are transmitted from the plurality of transducers at shifted timing or phase from each other (i.e., when sending electric signals to the plurality of transducers at a shifted timing or phase), it may be necessary to have a plurality of transmission circuits or change-over circuits. However, in this embodiment, because ultrasonic waves of the same phase are simply transmitted simultaneously from the plurality of transducers 22a-22l, it can achieve a configuration in which one transmission circuit 5 is connected to the plurality of transducers 22a-22l. Therefore, the circuit configuration of the transmission end will be comparatively simple, and, as a result, its cost can be reduced.

In addition, because the ultrasonic waves are simultaneously transmitted from the plurality of transducers 22a-22l to detect the bone shape, the time required for the shape detection can be shortened compared with the case where the bone shape is detected by transmitting the ultrasonic waves from the plurality of transducers with the shifted wave transmission timing. Therefore, shifting in the position of the ultrasonic transceiver 2 can be reduced during the transceiving of the ultrasonic waves and, thereby the bone shape can be detected with sufficient accuracy.

In addition, because the plurality of transducers 22a-22l are configured so as to perform both transmission and reception of the ultrasonic wave, the number of transducers used for the transmission and reception of the ultrasonic wave for detecting the shape of the bone 10 can be reduced, and the cost can be reduced as well.

Speed of Sound Deriving Step

Next, the speed-of-sound deriving module 83 derives a speed of sound in the bone 10 using the received wave signals of the arrayed transducer 22 when transmitting the ultrasonic wave from a transducer 21 dedicated to wave transmission, and the shape of the bone front surface 10a derived by the shape deriving module 82d. First, based on the shape of the bone front surface 10a, a transducer which receives a leaky surface wave is identified from the plurality of transducers 22a-22l (S21). Hereinafter, it will be explained particularly.

Figure 9:
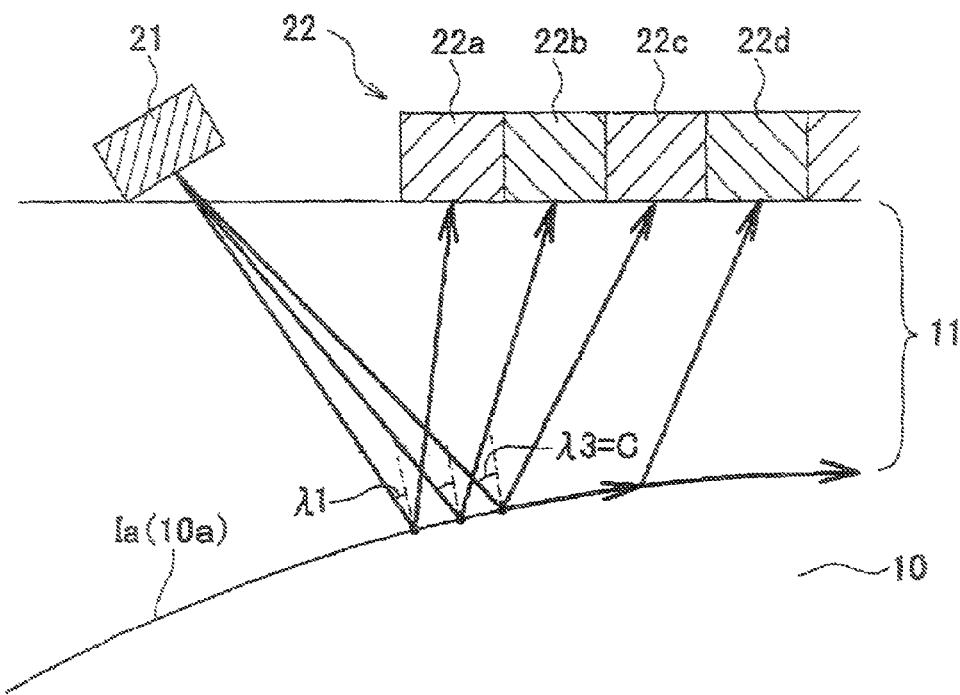
FIG. 9 is a schematic view for illustrating a method to identify a transducer which receives a leaky surface wave.

As shown in FIG. 9, based on the spatial relationship of the transducer 22a, the transducer 21 dedicated to wave transmission, and the bone front surface line Ia, a propagation course of the reflected wave from the bone front surface 10a that reaches the transducer 22a is detected using Fermat's principle. Fermat's principle states that an acoustic wave which passes through two points propagates through the shortest course among the possible ones. According to Fermat's principle, the propagation course of the reflected wave that reaches the transducer 22a will be the shortest course where a propagation distance from the transducer 21 dedicated to wave transmission to the transducer 22a among the propagation courses of the reflected wave which can be estimated within a range of directivity of the transducer 21 dedicated to wave transmission.

Next, the angle of incidence $\lambda 1$ between the bone front surface 10a and the reflected wave that reaches the transducer 22a is calculated. Then, from the assumed value Vb' of the speed of sound in the bone 10 and the speed of sound Vs in the soft tissues 11, an assumed value C of a critical angle is calculated so that this assumed value C of the critical angle and the angle of incidence $\lambda 1$ are compared. When the angle of incidence $\lambda 1$ is smaller than the assumed value C of the critical angle, a similar calculation is performed for each following transducers (the transducer 22b and the transducers on the right of the transducer 22b), in the order of the closest to the farthest from the transducer 21 dedicated to wave transmission, until the angle of incidence is equal to (or greater than) the assumed value C of the critical angle. Here, the angle of incidence $\lambda 3$ in the propagation course of the reflected wave that reaches the transducer 22c is assumed to be equal to the assumed value C of the critical angle. When the angle of incidence is equal to the critical angle, a surface wave occurs on the bone front surface 10a. Therefore, the transducer 22d is identified as the closest transducer to the transducer 21 dedicated to wave transmission that receives a leaky surface wave. That is, the transducer 22d and the transducers on the right of the transducer 22d are identified as the transducers which receive the leaky surface wave.

Note that, as described above, when the bone width (a diameter of the bone 10 in the horizontal direction of FIG. 1) is small, a transducer at a position apart from the transducer 21 dedicated to wave transmission (for example, the transducers 22k and 22l), may not be reached by the leaky surface wave. In this case, the closest transducer to the transducer 21 dedicated to wave transmission that receives the leaky surface wave may be identified by the above-described method, and the last transducer reached by the leaky surface wave may be identified using the bone front surface line Ia (that is, a transducer capable of receiving the leaky surface waver, which is most distant from the transducer 21 dedicated to wave transmission, may be identified).

Next, a waveform of the leaky surface wave (or the bone front-surface refracted wave) is detected from the received wave signals within a predetermined period of time from the wave transmission, measured by transducers 22d-22l identified as the transducers which receive the leaky surface wave (S22). Hereinafter, this will be explained in detail.

Figure 10:
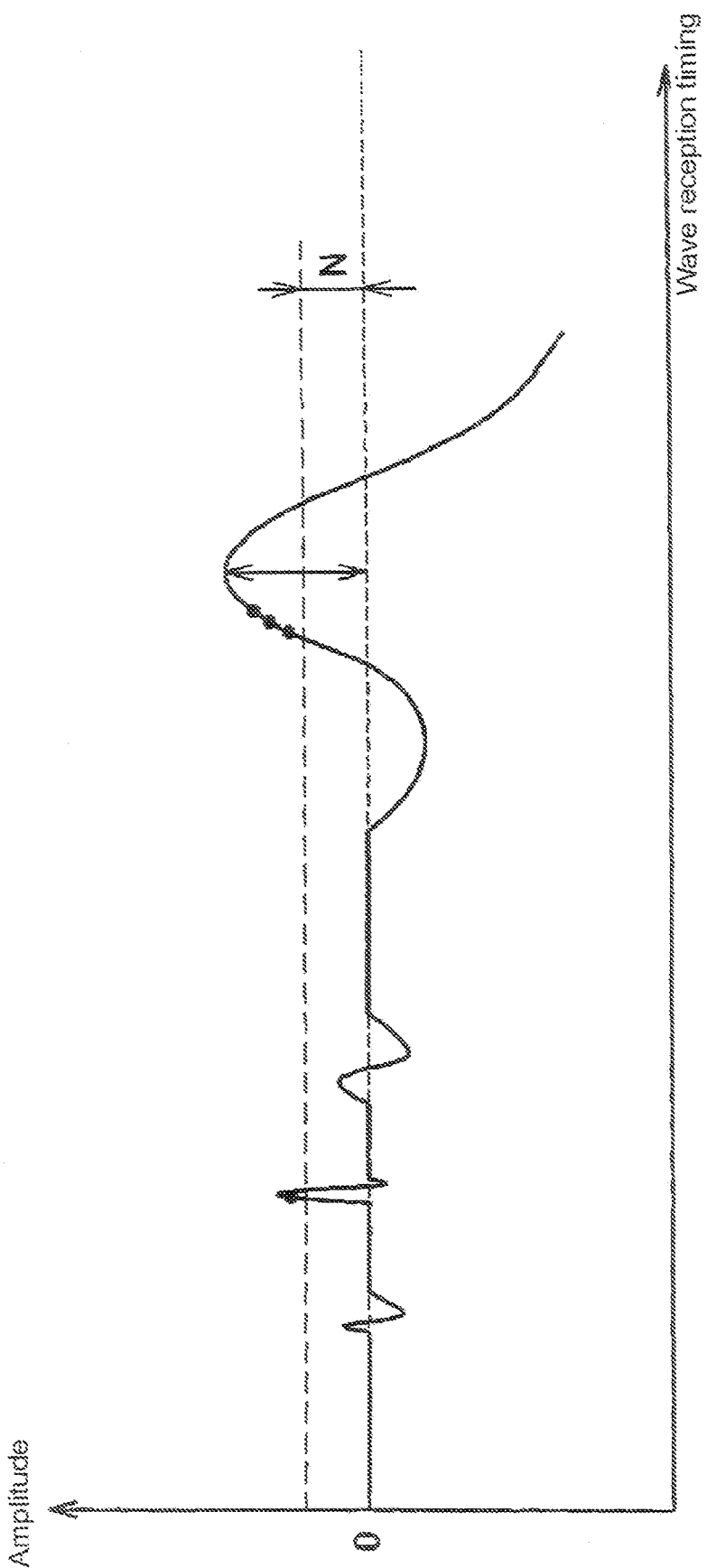
FIG. 10 is a graph for illustrating a method to distinguish a waveform of noise from a waveform of the ultrasonic wave.

Among the wave signals received by transducers 22d-22l, a waveform of the ultrasonic wave and a waveform of noise are distinguished to detect a waveform of the ultrasonic wave at the earliest wave-reception timing. Specifically, as shown in FIG. 10, a noise threshold N which is slightly greater than a general noise level is set, and when amplitude exceeds the threshold N consecutively at n points (for example, three points), it is determined to be a waveform of the ultrasonic wave, for example.

As described above, when both the leaky surface wave and the reflected wave from the bone front surface 10a reach one transducer, the leaky surface wave reaches before the reflected wave. Thus, by detecting the waveform of the ultrasonic wave at the earliest wave-reception timing, the waveform of the leaky surface wave or the bone front-surface refracted wave can be detected. The propagation time of the leaky surface wave or the bone front-surface refracted wave which reached each of the transducers 22d-22l can be derived from the waveform maximum peak value, the zero-crossing value, etc. Note that, although the direct wave may reach before the reflected wave and the leaky surface wave, because the direct wave is designed so that amplitude of which may be very small compared with the reflected wave and the leaky surface wave as described above, the direct wave may be hardly detectable.

Next, the circumferential speed of sound of the bone front surface 10a is calculated using the received wave signal of the ultrasonic wave at the earliest wave-reception timing (the received wave signal of the leaky surface wave or the bone front-surface refracted wave) of the transducers 22d-22l which are identified as transducers which receive the leaky surface wave, and the shape of the bone front surface 10a (S23).

Figure 11:
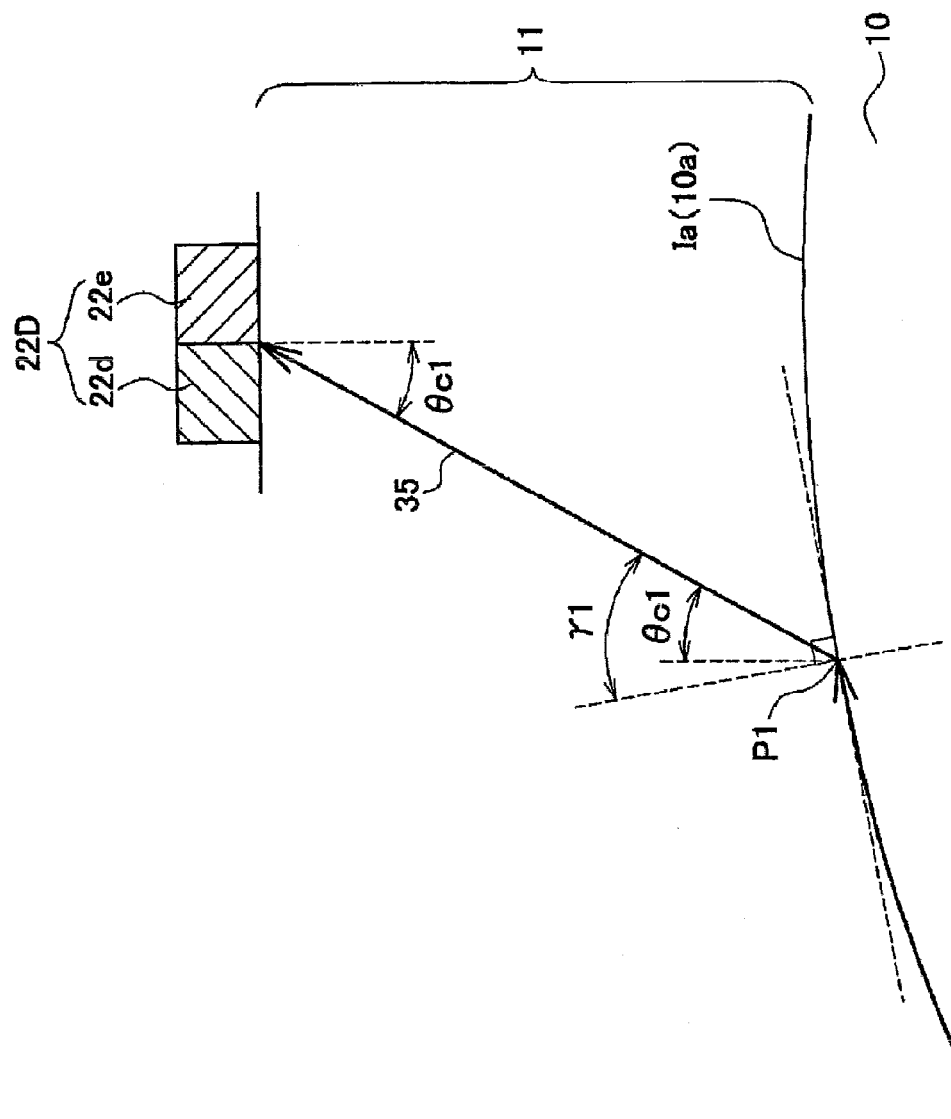
FIG. 11 is a schematic view for illustrating a deriving method of a speed of sound.

First, one transducer group is selected from the plurality of transducers 22d-22l identified as transducers which receive the leaky surface wave. Hereinafter, as shown in FIG. 11, a case where the transducer group 22D having the transducers 22d and 22e is selected will be explained as an example.

First, the waveform of the ultrasonic wave at the earliest wave-reception timing detected from the received wave signals of the transducers 22d and 22e (a waveform of the leaky surface wave or the bone front-surface refracted wave) is assumed to be the waveform of the leaky surface wave. The angle of refraction of the bone surface refracted wave from the bone front surface 10a is very close to the angle of refraction of the leaky surface wave from the bone front surface 10a (the same angle as the critical angle). Therefore, even if the waveform of the ultrasonic wave at the earliest wave-reception timing is a waveform of the bone front-surface refracted wave, the speed of sound can be derived with sufficient accuracy.

It is assumed that the incoming directions of the leaky surface waves that reach the two transducers 22d and 22e approximate with each other, and an incoming angle $\theta c1$ of the leaky surface wave 35 with respect to the transducer group 22D is detected from the time difference between the received wave signals of the leaky surface waves of the two transducers 22d and 22e. As a particular method of detecting the incoming angle $\theta c1$, a similar method to the method of detecting the incoming angles $\theta a$ and $\theta b$ by the incoming angle detecting module may be used (refer to FIG. 6B).

An originating point P1 of the leaky surface wave 35 on the bone front surface 10a is detected from the incoming angle $\theta c1$ and the bone front surface line Ia. An outgoing angle $\gamma 1$ of the leaky surface wave 35 from the bone front surface 10a is calculated from the normal direction at the point P1 on the bone front surface line Ia and the incoming angle $\theta c1$. If a speed of sound in the bone 10 is set to Vb, a relation of $Vb=Vs/\sin \gamma 1$ can be satisfied by the Snell's law. From this equation, the speed of sound Vb of the ultrasonic wave (particularly, the surface wave) that propagates along the bone front surface 10a in the circumferential direction can be calculated.

For all or some selected transducer groups among the plurality of the transducer groups 22E-22K, the speed of sounds Vb in the bone 10 are calculated similarly, and an average value of the plurality of speed of sounds Vb is then calculated. Thus, the speed of sound in the bone 10 can be derived with sufficient accuracy. The speed of sounds Vb derived for the transducer groups 22E-22K can also be mapped on the bone front surface line Ia.

As described above, the speed of sound in the bone 10 is calculated using the information on the shape of the bone front surface 10a. Therefore, even if the shape of the bone front surface 10a is curved, or even if the bone shape inclines to the contacting face 2a, the speed of sound in the bone 10 can be derived with sufficient accuracy. As a result, a diagnostic accuracy of bone strength can be improved.

As described above, although the circumferential speed of sound is derived, alternatively, the ultrasonic transceiver 2 may be installed so that the arrayed direction of the arrayed transducer 22 is substantially in agreement with the longitudinal direction of the bone 10 to derive the longitudinal speed of sound. Note that, because the same bone thickness derived when the cross-sectional shape perpendicular to the longitudinal direction of the bone 10 is derived is used for the thickness of the bone 10, the shape of the bone back surface 10b does not need to be additionally derived in this case.

Finally, after the speeds of sounds in the both directions are detected (S23B), the bone strength index deriving module 84 derives an index related to the bone strength using the circumferential speed of sound and the longitudinal speed of sound which are derived by the speed-of-sound deriving module 83, and the shapes of the bone front surface 10a and the bone back surface 10b detected by the shape detecting module 82 (the shape deriving module 82d) (S24). The derived index is displayed on the display module 9.

As described above, the bone strength diagnostic device 1 can obtain the thickness of the bone 10, the image of the bone 10, the circumferential speed of sound, and the longitudinal speed of sound, as the indexes of bone strength or elements for deriving the indexes of bone strength.

Bone has an anisotropy structure in which it is stronger in the direction of loads. In a macroscale, the bone has a long tubular-shaped femur, tibia, or radius, and it has a structure strong against the load direction. In a microscale, bone has pores of substantially a circular cylinder shape of tens to hundreds of microns. The pores extend substantially in the load direction and, thus, the bone has a structure strong against the load direction. In a nanoscale, bone has a structure in which biological apatite crystals surround collagen fibers. The c-axis of collagen fibers or biological apatite crystals is often oriented in the load direction. Thus, it is important to examine the bone anisotropy structure when diagnosing bone strength.

Recently, it has been said that the bone strength can be expressed with two factors, the bone mass and the bone quality. In addition to the bone size (outer diameter) and the bone thickness which represent the bone mass, examining the anisotropy structure leads to diagnosis of the bone quality.

First, for the bone strength, the bone size (outer diameter) and the cortical bone thickness that constitute the macro structure of a cortical bone are important factors. As described above, the shape deriving module 82d derives the thickness of the cortical bone 10 based on the detected shapes of the bone front surface 10a and the bone back surface 10b, and estimates the size (outer diameter) of the bone 10. Therefore, the index related to the bone mass can be derived by using the thickness of the cortical bone 10 and the size of the bone 10.

The speed of sound of the ultrasonic wave that propagates along the bone surface in the circumferential direction is greatly affected by a percentage of pores, a pore size, and a pore connectivity that constitute the micro structure of cortical bone. These are factors related to the bone density of the cortical bone. Therefore, the index related to the bone density can be derived by using the circumferential speed of sound.

On the other hand, the speed of sound of the ultrasonic wave that propagates along the bone surface in the longitudinal direction is influenced by both the orientation of the biological apatite crystals that constitute the nanostructure of cortical bone, and the bone density or pores that constitute the bone micro structure. Therefore, the bone anisotropy structure cannot be estimated only with the longitudinal speed of sound, and the latter is insufficient for the diagnostic index of bone strength. The index related to the bone orientation can be derived by using both the longitudinal speed of sound and the circumferential speed of sound.

The speed of sound V of the ultrasonic wave which passes through inside of an object can be expressed by the following Equation (1), indicating an elastic characteristic of the bone.

$$V = c\sqrt{c/\rho} \tag{1}$$

Here, c is elastic stiffness and $\rho$ is density.

Therefore, the circumferential speed of sound and the longitudinal speed of sound may also be used as the indexes of the bone strength as they are. Because the speed of sound V represents an average elastic characteristic at both of the micro- and the nano-structure, it is characterized in that it can directly show the index of the bone quality related to the bone strength, unlike with X-rays.

As described above, because the bone strength diagnostic device 1 can derive the plurality of indexes related to the bone strength, it is possible to diagnose bone strength in more detail by using these indexes. Note that only one or some of the indexes may be used in this embodiment without using all of the indexes as the index of bone strength.

Modified Embodiments

Next, modified embodiments to which various changes is made to the previous embodiment will be explained. However, components having a similar configuration to those of the previous embodiment are given with the same reference numerals, and their explanation will be suitably omitted.

Modified Embodiment 1

In the previous embodiment, both the circumferential speed of sound and the longitudinal speed of sound are derived. However, the bone strength may be diagnosed by deriving only the circumferential speed of sound (the thickness of the cortical bone 10).

Modified Embodiment 2

The calculation module 8 may include a damping coefficient detecting module that detects a damping coefficient of the ultrasonic wave received by each transducer based on the transmitted wave signal of the transducer 21 dedicated to wave transmission and the received wave signal of each of the transducers 22a-22l. A particular operation in this modified embodiment is explained below.

First, the damping characteristic detecting module calculates a spectrum of the leaky surface wave (or the bone front-surface refracted wave) received by each of the transducers 22a-22l and a spectrum of the ultrasonic wave transmitted from the transducer 21 dedicated to wave transmission with the Fourier transform to detect a spectrum ratio of the received wave signal of each of the transducers 22a-22l with respect to the transmitted wave signal.

Generally, because the attenuation rate of the ultrasonic wave that propagates inside of a living body is greater in high-frequency components of the ultrasonic wave than low-frequency components, the detected spectrum ratio has a certain inclination. By calculating this inclination, a damping coefficient (BUA: Broadband Ultrasonic Attenuation [dB/MHz]) can be detected.

The detected damping coefficients (BUA) of the plurality of transducers 22a-22l are displayed on the display module 9.

By using the damping coefficients (BUA) of the plurality of transducers 22a-22l, the bone strength can be diagnosed in more detail.

Modified Embodiment 3

The maximum amplitudes of the leaky surface waves (or the bone front-surface refracted waves) received by the transducers 22a-22l may be displayed on the display module 9, for example, and the bone strength may be diagnosed using these amplitudes.

Modified Embodiment 4

Figure 12:
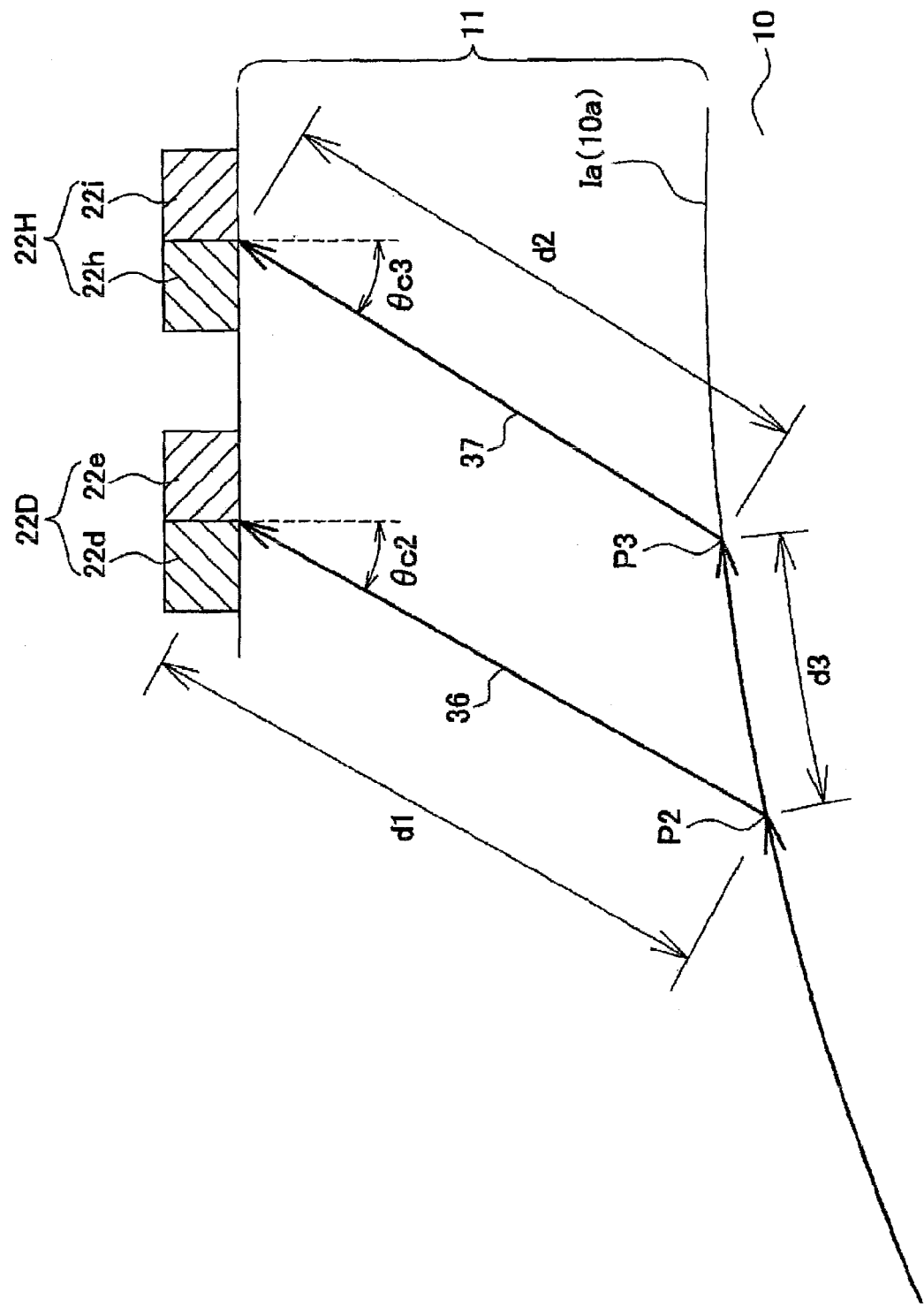
FIG. 12 is a schematic view for illustrating a deriving method of the speed of sound according to Modified Embodiment 4.

As the method of deriving the speed of sound in the bone 10, the following method may also be used. First, two transducer groups (i.e., two groups of transducers, each including a pair of transducers) are selected from the plurality of transducers identified as transducers that receive the leaky surface wave. Preferably, the transducers to be selected do not overlap within the same transducer group or over the transducer groups. Hereinafter, as shown in FIG. 12, a case where the transducer group 22D having the transducers 22d and 22e, and the transducer group 22H having the transducers 22h and 22i are selected will be explained as an example.

Similar to the previous embodiments, assuming that the waveform of the leaky surface wave or the bone front-surface refracted wave detected from the received wave signals of the transducers 22d, 22e, 22h, and 22i is the waveform of the leaky surface wave, The incoming angles θc2 and θc3 of the leaky surface waves 36 and 37 to the two transducer groups 22D and 22H are detected, respectively.

The originating points P2 and P3 of the leaky surface waves 36 and 37 in the bone front surface 10a are detected from the incoming angles θc2 and θc3, and the bone front surface line Ia, respectively. Then, a distance d1 from the transducer group 22D to the point P1, a distance d2 from the transducer group 22H to the point P2, and a distance d3 between the points P1 and P2 are calculated.

When the time difference between the times at which the two transducer groups 22D and 22H received the leaky surface waves 36 and 37 is set to ΔTc, the time difference ΔTc can be expressed by ΔTc=(d3/Vb)−{(d1−d2)/Vs} from the difference in the propagation routes of the ultrasonic wave that reaches the two transducer groups 22D and 22H. The ΔTc can be calculated using the wave-reception timings of the leaky surface wave of the four transducers 22d, 22e, 22h, and 22i. Therefore, the speed of sound Vb in the bone 10 can be calculated from the equation of Vb=d3/{ΔTc+(d1−d2)/Vs}.

Modified Embodiment 5

As the method of deriving the speed of sound in the bone 10, the following methods may also be used. First, one transducer group is selected from the plurality of transducers identified as transducers that receive the leaky surface wave. Hereinafter, as shown in FIG. 13, a case where the transducer group 22D having the transducers 22d and 22e is selected is explained as an example.

Assuming that the waveform of the leaky surface wave or the bone front-surface refracted wave detected based on the received wave signals of the transducers 22d and 22e is the waveform of the bone front-surface refracted wave, an incoming angle θc4 of the bone front-surface refracted wave 38 with respect to the transducer group 22D is calculated. Then, from the incoming angle θc4 and the bone front surface line Ia, an outgoing point (refracted point) P4 of the bone front-surface refracted wave 38 in the bone front surface 10*a* is detected. Then, an outgoing angle (angle of refraction) γ4, between the bone front-surface refracted wave 38 and the normal direction at the point P4 on the bone front surface line Ia, is calculated from the incoming angle θc4 and the angle of the surface line Ia with the horizontal axis.

The bone front-surface refracted wave 38 that propagates inside of the bone is generated by an ultrasonic wave 39 refracted on the bone front surface 10*a*. When an angle of incidence of the ultrasonic wave 39 to the bone front surface 10*a* is φ, the speed of sound Vb in the bone 10 (i.e., the speed of sound of the ultrasonic wave 39) can be expressed by Vb=Vs−sin φ/sin γ4 by the Snell's law.

Figure 13:
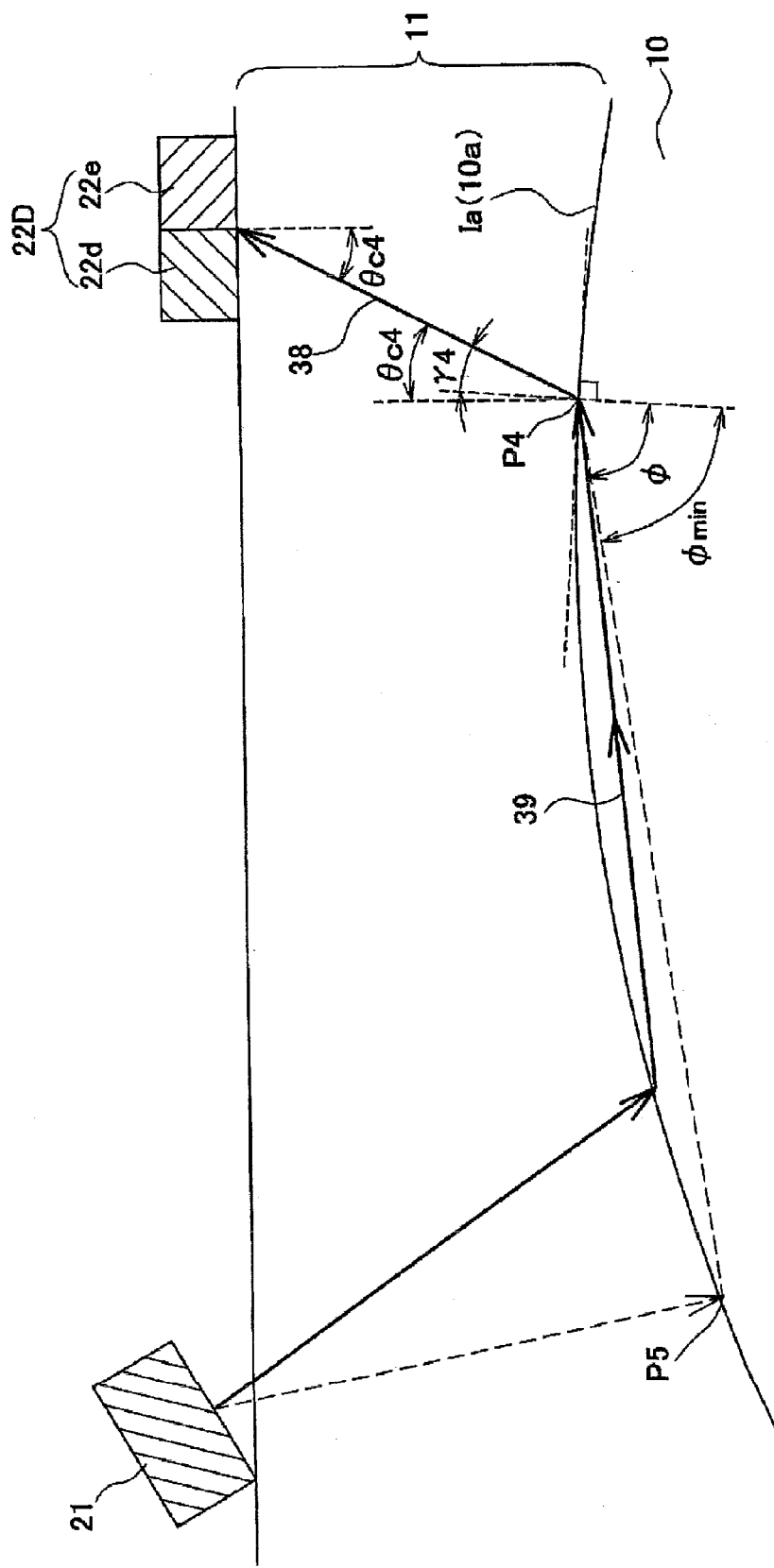
FIG. 13 is a schematic view for illustrating a deriving method of the speed of sound according to Modified Embodiment 5.

Next, based on the angle range of the ultrasonic wave transmitted from the transducer 21 dedicated to wave transmission, a position P5 of the left end part in FIG. 13 is detected within the incident range of the ultrasonic wave on the bone front surface 10*a*. An angle of incidence φmin is calculated assuming that the ultrasonic wave 39 propagates from the point P5 to the point P4. The point P5 can be at a position beyond the range of the bone shape derived by the shape deriving module 82*d*. In this case, the point P5 is detected using the bone shape predicted from the bone shape within the range derived by the shape deriving module 82*d*.

Figure 14:
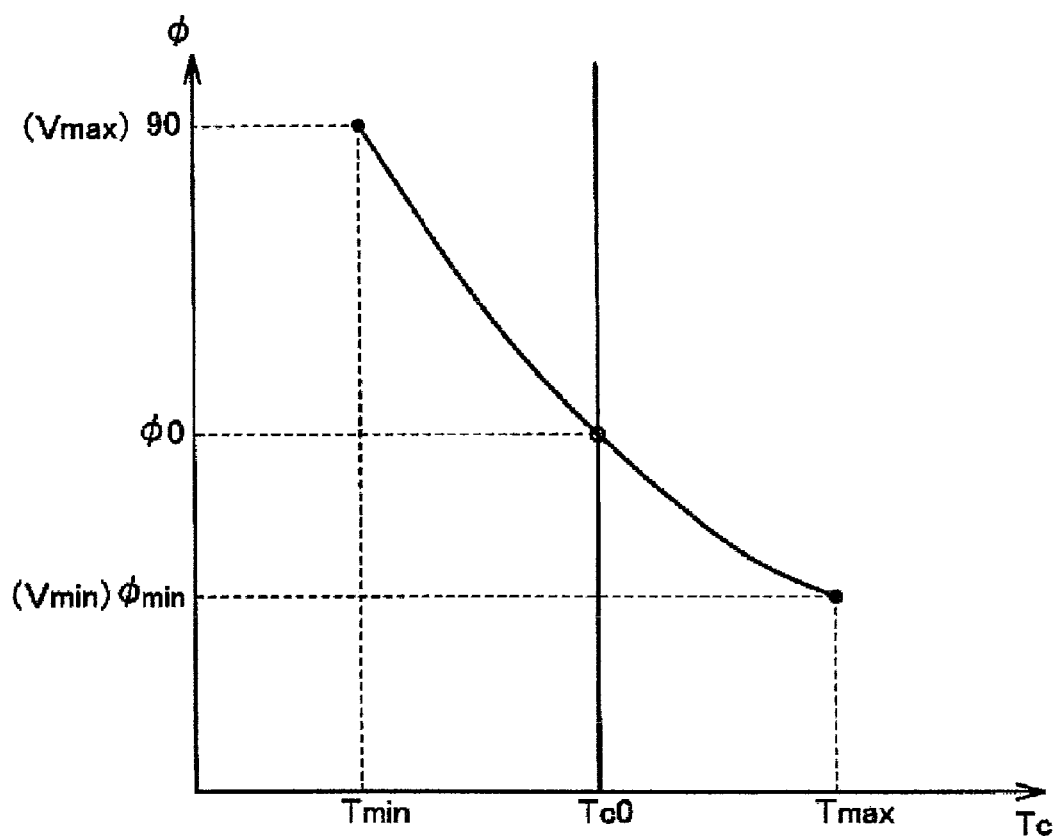
FIG. 14 is a graph to be used for deriving the speed of sound by Modified Embodiment 5, showing a relation between an angle of incidence and a propagation time.

The angle of incidence φ is an angle within a range from φmin to 90 degrees. The speed of sound Vb is a speed ranging from Vmin (Vmin=Vs*sin φmin/sin γ4) to Vmax (Vmax=Vs/sin γ4). FIG. 14 is a graph showing a relation between the angle of incidence φ and a propagation time Tc from wave transmission to wave reception. The curve in FIG. 14 shows the propagation time Tc in the propagation course of each angle of incidence φ when changing the angle of incidence φ from φmin to 90 degrees. The propagation time Tc at a certain angle of incidence φ is calculated from the propagation course length according to the angle of incidence φ, the speed of sound Vb in the bone according to the angle of incidence φ, and the speed of sound Vs in the soft tissues.

An actual measurement Tc0 of the propagation time is calculated from the received wave signals of the transducers 22*d* and 22*e*. An angle of incidence φ0 is derived from an intersecting point of the curve of FIG. 14 and the line of Tc=Tc0. The speed of sound Vb in the bone 10 is calculated using the angle of incidence φ0. Thus, the speed of sound Vb of the ultrasonic wave that propagates inside of the bone 10 in the circumferential direction (particularly, the ultrasonic wave that propagates in the vicinity of the bone front surface 10*a* of the bone 10) can be derived.

Modified Embodiment 6

In the previous embodiments, an ultrasonic wave is transmitted from the arrayed transducer 22, and after a predetermined period of time after that, another ultrasonic wave is transmitted from the transducer 21 dedicated to wave transmission. However, the ultrasonic waves may be simultaneously transmitted from the arrayed transducer 22 and the transducer 21 dedicated to wave transmission.

In this case, different transmission circuits may be connected to the arrayed transducer 22 and the transducer 21 dedicated to wave transmission, so that ultrasonic waves of different frequencies may be transmitted from the arrayed transducer 22 and the transducer 21 dedicated to wave transmission.

Modified Embodiment 7

Figure 15A:
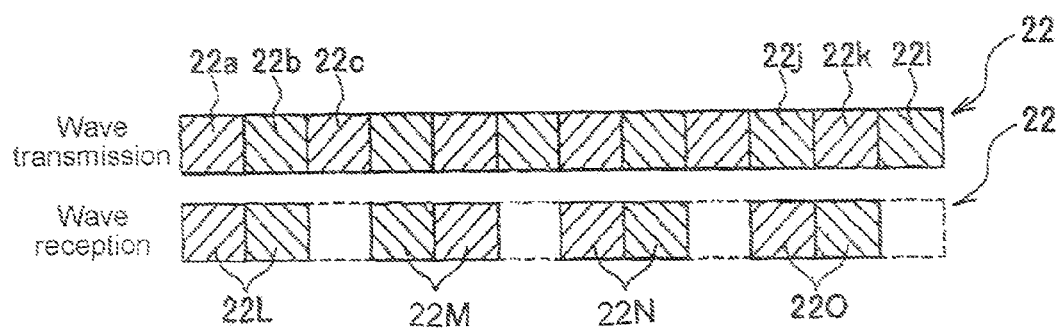
FIGS. 15A to 15C are schematic views of arrayed transducers, where

Although the plurality of transducers that constitute the arrayed transducer 22 perform both wave transmission and wave reception in the previous embodiments, only some transducers among the twelve transducers 22*a*-22*l* may be configured so as to perform the reception of the ultrasonic wave. Particularly, for example, as shown in FIG. 15A, eight transducers 22*a*, 22*b*, 22*d*, 22*e*, 22*g*, 22*h*, 22*j*, and 22*k* among the twelve transducers 22*a*-22*l* may be connected with eight reception circuits to respectively perform the wave reception of the ultrasonic waves (the number of transducers may depend on the configuration of the arrayed transducer). In this case, the incoming direction detecting module 82*a* may determine four transducer groups 22L-22O where each transducer group is constituted with two adjacent transducers.

Modified Embodiment 8

Figure 15B:
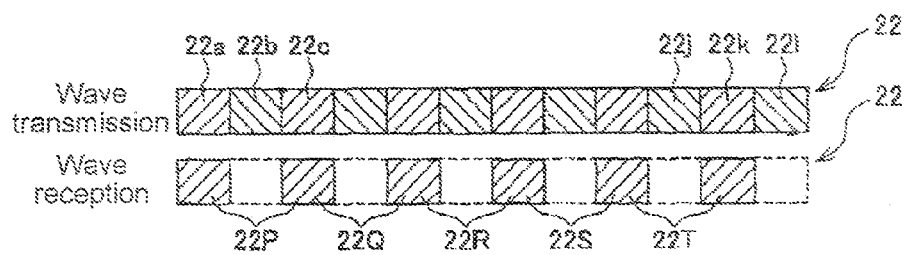

Moreover, for example, as shown in FIG. 15B, alternately selected six transducers from the twelve transducers 22*a*-22*l* (for example, the transducers 22*a*, 22*c*, 22*e*, ..., and 22*k*) may only perform wave reception of the ultrasonic wave (the number of transducers may depend on the configuration of the arrayed transducer). In this case, the incoming direction detecting module 82*a* may determine five sets of transducers 22P-22T where alternately selected two transducers constitute a transducer group.

According to the configurations of the Modified Embodiments 7 and 8, the number of reception circuits can be reduced comparing to the previous embodiments and, thus, the circuit configuration will be simplified and its cost can be reduced as well.

Modified Embodiment 9

Figure 15C:
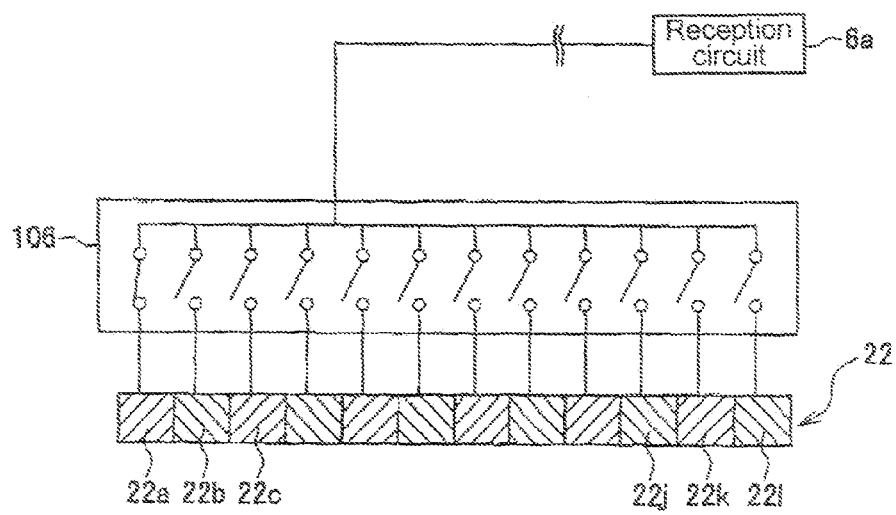

A change-over circuit, such as an analog switch, may be provided between the reception circuit and the arrayed transducer 22, and only some transducers among the twelve transducers 22*a*-22*l*, which are connected to the reception circuit through the change-over circuit may perform wave reception (the number of transducers may depend on the configuration of the arrayed transducer). For example, as shown in FIG. 15C, only one transducer among the twelve transducers 22*a*-22*l* may be connected to the reception circuit 6*a* through the change-over circuit 106.

The change-over circuit 106 switches over sequentially from one transducer to another, which is connected to the reception circuit, each time an ultrasonic wave is transmitted. By transmitting the ultrasonic waves a total of twelve times, the received wave signals of the twelve transducers 22*a*-22*l* can be acquired. Note that an illustration of a circuit configuration of the transmission end is omitted in FIG. 15C. According to this configuration, the number of reception circuits can be reduced compared to the previous embodiments and, thus, its cost can be reduced, while the received wave signals of the twelve transducers 22*a*-22*l* can be acquired similar to the previous embodiments.

Modified Embodiment 10

In the previous embodiments, the plurality of transducers 22*a*-22*l* constituting the arrayed transducer 22 perform both wave reception of the ultrasonic wave transmitted from the arrayed transducer 22 and wave reception of the ultrasonic wave transmitted from the transducer 21 dedicated to wave transmission. However, without limiting to this configuration, for example, four transducers 22*a*-22*d* on the side of the transducer 21 dedicated to wave transmission may perform only wave reception of the ultrasonic wave transmitted from the arrayed transducer 22, and four transducers 22*j*-22*l* on the opposite side from the transducer 21 dedicated to wave transmission may perform only wave reception of the ultrasonic wave transmitted from the transducer 21 dedicated to wave transmission, and further, four transducers 22e-22h of the central part may perform wave reception in both cases of wave transmission (the division in number of the transducers is not intended to be limited and therefore any number can be selected to divide the transducers in group).

In this case, eight reception circuits may be provided, and a change-over circuit may be provided between the eight reception circuits and the arrayed transducer 22. In addition, the transducer that performs wave reception may be switched according to the transducer that transmits the ultrasonic wave (the transducer 21 dedicated to wave transmission or the arrayed transducer 22). According to this configuration, the number of reception circuits can be reduced compared to the previous embodiments.

Modified Embodiment 11

Without providing the transducer 21 dedicated to wave transmission, an ultrasonic wave may be transmitted obliquely to the contacting face 2a by transmitting the ultrasonic wave whose phase may be controlled from the plurality of (for example, four) transducers at the end of the arrayed transducer 22.

According to this configuration, because the transducer 21 dedicated to wave transmission is unnecessary, the configuration of the ultrasonic transceiver 2 includes only the arrayed transducer 22 and, thus it can be simplified. Further, because the transducer 21 dedicated to wave transmission is not provided, the number of transducers that constitute the arrayed transducer 22 can be increased. Therefore, the range in which the bone shape can be detected will be wider. However, in this configuration, a plurality of transmission circuits is needed and the circuit configuration will be more complicated with an increased cost. Thus, the previous embodiments may be more preferred for this regards.

Modified Embodiment 12

Figure 16A:
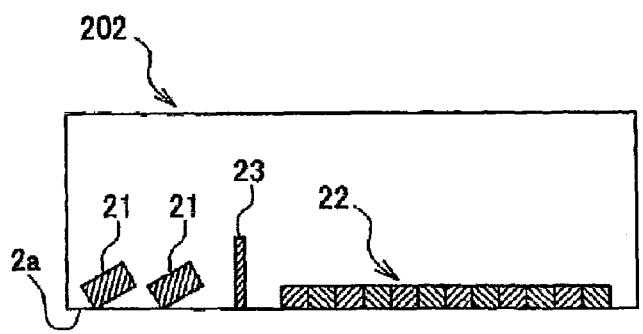
FIGS. 16A to 16C are views showing configurations of ultrasonic transceivers, where

In the ultrasonic transceiver 2 of the previous embodiments, although the number of transducers 21 dedicated to wave transmission is one, this transceiver 2 may be an ultrasonic transducer 202 including two transducers 21 dedicated to wave transmission arranged in the same direction as the arrayed direction of the arrayed transducer 22 as shown in FIG. 16A, for example. In this configuration, transducers that transmit an ultrasonic wave are selected from the two transducers 21 dedicated to wave transmission according to the thickness of the soft tissues 11 and/or the size of the curvature of the bone front surface 10a. According to this configuration, the arrayed transducer 22 can receive the leaky surface wave or the bone front-surface refracted wave more reliably.

Modified Embodiment 13

Figure 16B:
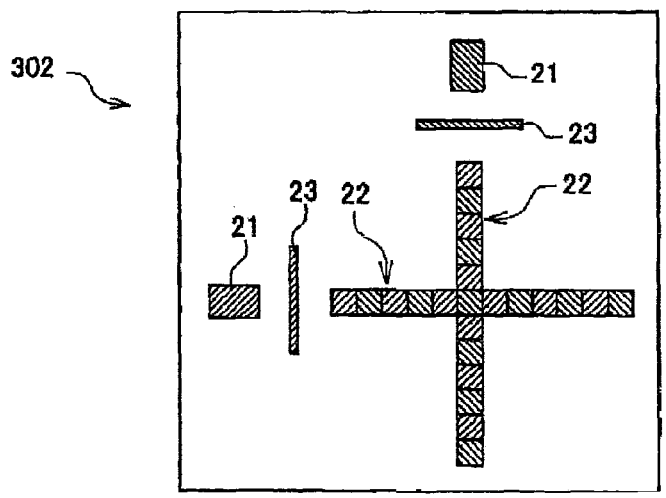

Similarly, for example, as shown in FIG. 16B, the ultrasonic transceiver 2 may be an ultrasonic transceiver 302 including two arrayed transducers 22 arranged perpendicularly to each other, and two transducers 21 dedicated to wave transmission arranged at the ends of the arranged direction of these two arrayed transducers 22. FIG. 16B is a plan view looking toward the contacting face 2a.

According to this configuration, without changing the orientation of the ultrasonic transceiver 302, a cross-sectional shape of the bone in the circumferential direction and a cross-sectional shape in the longitudinal direction can be detected, and the circumferential speed of sound and the longitudinal speed of sound can be derived as well. Therefore, the measuring time can be shortened.

Modified Embodiment 14

Figure 16C:
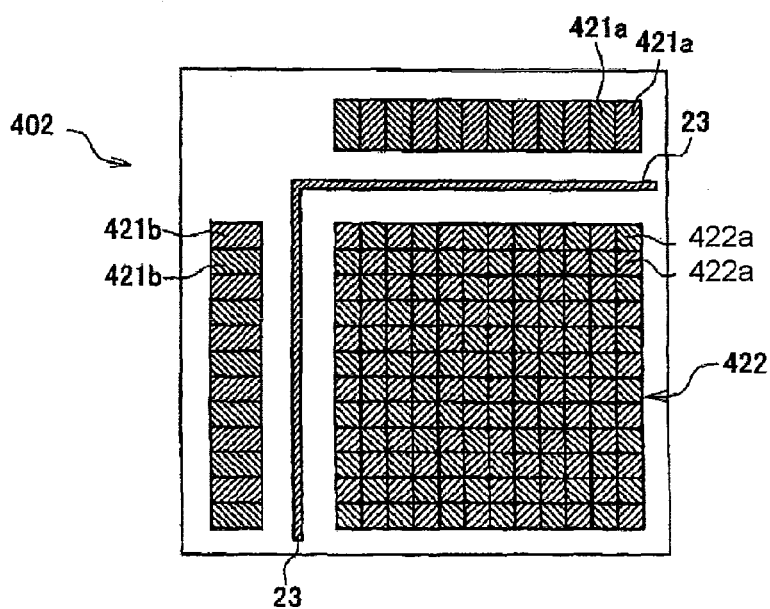
Figure 17A:
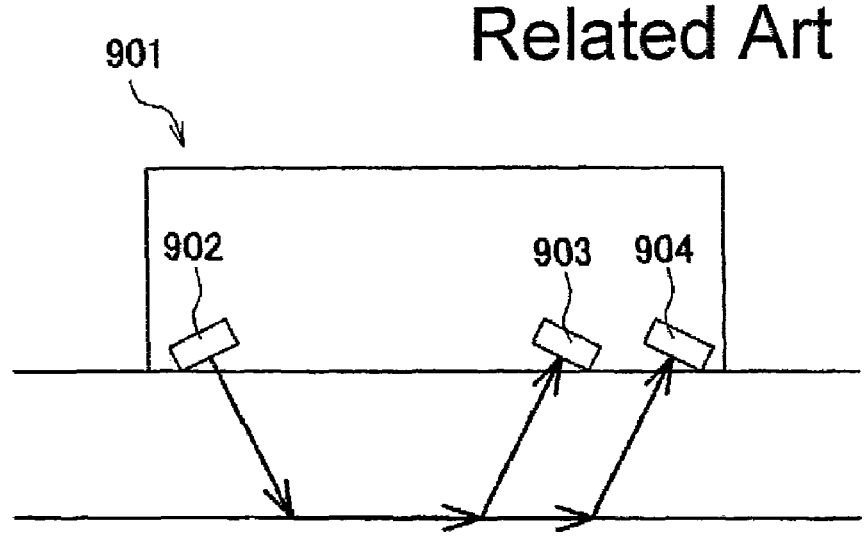
FIGS. 17A and 17B are schematic views showing conventional speed-of-sound measuring devices.
Figure 17B:
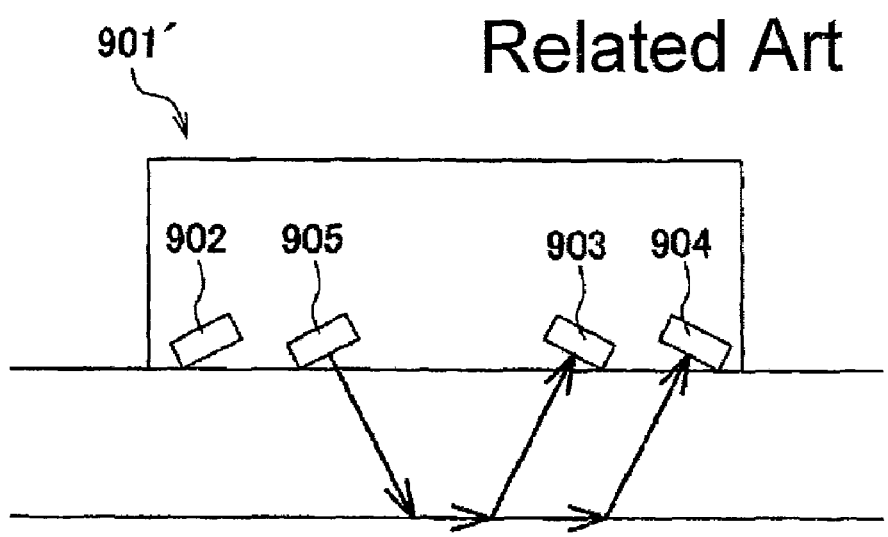

For example, the ultrasonic transceiver 2 may be an ultrasonic transceiver 402 including an arrayed transducer 422 having a plurality of transducers 422a arranged in a 12×12 matrix as shown in FIG. 16C. In this figure, twelve transducers 421a dedicated to wave transmission are arranged in the left-and-right direction in the upper part of the arrayed transducer 422 and twelve transducers 421b dedicated to wave transmission are arranged in the up-and-down direction on the left-hand side of the arrayed transducer 422 Note that the number of transducers may depend on the configuration of the ultrasonic transceiver 2.

According to this configuration, for example, from the right end of the matrix-arrayed transducer 422 in turn, using the twelve transducers 422a arranged in the up-and-down direction and the transducer 421a dedicated to wave transmission corresponding thereto, the bone shape is detected similar to the previous embodiments to derive the speed of sound in the bone using the detected bone shape. Accordingly, the three-dimensional shape of the bone 10 can be derived. In addition, the speed of sound of the ultrasonic wave that propagates in the up-and-down direction at the twelve locations in the left-and-right direction can be derived (between 421a and 422a). Therefore, because the speed of sound in a certain direction can be measured at a plurality of locations, the speed of sound of the ultrasonic wave in the bone can be derived with more accuracy.

The speed of sound of the ultrasonic wave that propagates in the left-and-right direction can be derived at twelve locations in the up-and-down direction by deriving sequentially from the upper end of the arrayed transducer 422, speeds of sound using the twelve transducers 422a arranged in the left-and-right direction and the transducer 421b dedicated to wave transmission corresponding thereto arranged in the up-and-down direction.

Modified Embodiment 15

The shape detection module that detects the shape of the front surface of the bone 10 is not limited to the configurations of the previous embodiments. For example, it may be or may not be of a type using the ultrasonic wave (for example, X-rays may be used instead). However, in the case described above in which the shape detection module uses the ultrasonic wave, a part of the configuration for deriving the speed of sound (for example, the transmission circuit, the reception circuit, etc.) may be commonly formed with the shape detection module, and thereby its cost can be reduced.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims, including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "approximately" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

What is claimed is:

1. A bone strength diagnostic device, comprising:
a wave-transmission module for deriving a speed of sound that transmits an ultrasonic wave from a wave-transmission transducer for deriving the speed of sound obliquely to a bone covered with soft tissues;
a wave-reception module for deriving the speed of sound that receives the ultrasonic wave that exits from the bone to the side of the soft tissues with a plurality of wave-reception transducers for deriving the speed of sound, the ultrasonic wave being received after it is transmitted from the wave-transmission module for deriving the speed of sound and propagates along a front surface of the bone;
a shape detection module for detecting a shape of the front surface of the bone; and
a speed-of-sound deriving module for deriving the speed of sound of the ultrasonic wave that propagates along the front surface of the bone based on the received wave signal by the wave-reception module for deriving the speed of sound, and the shape of the front surface of the bone detected by the shape detection module,
wherein the shape detection module includes:
a wave-transmission module for shape detection that transmits the ultrasonic wave to the bone;
a wave-reception module for shape detection that receives a front-surface reflected wave of the ultrasonic wave from the front surface of the bone, the ultrasonic wave being transmitted from the wave-transmission module for shape detection; and
a front surface shape detecting module for detecting the shape of the front surface of the bone using the wave signal received by the wave-reception module for shape detection,
wherein the wave-transmission module for shape detection includes a plurality of wave-transmission transducers for shape detection that transmit the ultrasonic waves simultaneously; and
wherein the wave-reception module for shape detection includes a plurality of wave-reception transducers for shape detection that receive the front-surface reflected wave; and
wherein the front surface shape detecting module includes:
an incoming direction detecting module for detecting an incoming direction of the front-surface reflected wave to each transducer group using a time difference between times when two wave-reception transducers for shape detection constituting each transducer group receive the front-surface reflected wave, each transducer group including adjacent two wave-reception transducers for shape detection among the plurality of wave-reception transducers for shape detection;
a propagation time detecting module for detecting a propagation time of the front-surface reflected wave that reaches each transducer group using the received wave signal of the front-surface reflected wave of at least one wave-reception transducer for shape detection among the two wave-reception transducers for shape detection constituting each transducer group;
a front-surface reflection point detecting module for detecting a plurality of reflection points of the ultrasonic wave on the front surface of the bone based on the incoming direction and the propagation time of the front-surface reflected wave detected for each transducer group by the incoming direction detecting module and the propagation time detecting module, respectively; and
a shape deriving module for deriving the shape of the front surface of the bone using the plurality of reflection points on the front surface of the bone, the reflection points being detected for the plurality of transducer groups having different transducers by the front-surface reflection point detecting module.

2. The bone strength diagnostic device of claim 1, wherein a sound insulating material is arranged between the wave-transmission module for deriving the speed of sound and the plurality of wave-reception transducers for deriving the speed of sound.

3. The bone strength diagnostic device of claim 1, wherein a wave-transmission transducer for shape detection from said plurality of wave-transmission transducers for shape detection, functions as a wave-reception transducer for shape detection from said plurality of wave-reception transducers for shape detection, as well.

4. The bone strength diagnostic device of claim 3, wherein a wave-reception transducer for deriving the speed of sound from said plurality of wave-reception transducers for deriving the speed of sound functions as a wave-reception transducer for shape detection from said plurality of wave-reception transducers for shape detection, as well.

5. The bone strength diagnostic device of claim 1, wherein a wave-reception transducer for deriving the speed of sound from said plurality of wave-reception transducers for deriving the speed of sound, functions as a wave-reception transducer for shape detection from said plurality of wave-reception transducers for shape detection, as well.

6. The bone strength diagnostic device of claim 1, wherein the shape detection module performs detection of a shape of a back surface of the bone in addition to the detection of the shape of the front surface of the bone.

7. The bone strength diagnostic device of claim 1, wherein the wave-reception module for shape detection performs wave reception of a back-surface reflected wave, that is reflected from the back surface of the bone and reaches the plurality of wave-reception transducers for shape detection after the front-surface reflected wave, in addition to performing the wave reception of the front-surface reflected wave;
  wherein the incoming direction detecting module performs detection of an incoming direction of the back-surface reflected wave to each transducer group using a time difference between times when the two wave-reception transducers for shape detection constituting each transducer group receives the back-surface reflected wave in addition to performing detection of the incoming direction of the front-surface reflected wave;
  wherein the propagation time detecting module performs detection of the propagation time of the back-surface reflected wave that reaches each transducer group using the received wave signal of the back-surface reflected wave of at least one wave-reception transducer for shape detection among the two wave-reception transducers for shape detection constituting each transducer group in addition to performing the detection of the propagation time of the front-surface reflected wave that reaches each transducer group;
  wherein the shape detecting module includes a back-surface reflection point detecting module for detecting a reflection point of the ultrasonic wave on the back surface of the bone based on the incoming direction and the propagation time of the back-surface reflected wave detected for each transducer group by the incoming direction detecting module and the propagation time detecting module, and the shape of the front surface of the bone derived by the shape deriving module; and
  wherein the shape deriving module derives the shape of the back surface of the bone with the back-surface reflection point detecting module using the plurality of reflection points on the back surface of the bone that are detected for the plurality of transducer groups having different transducers.

8. The bone strength diagnostic device of claim 1, further comprising a damping coefficient detecting module for detecting a damping coefficient of the ultrasonic wave received by the wave-reception module for deriving the speed of sound based on the transmitted wave signal of the wave-transmission module for deriving the speed of sound and the received wave signal of the wave-reception module for deriving the speed of sound.

9. The bone strength diagnostic device of claim 1, wherein the shape detection module performs detection of a shape of a back surface of the bone in addition to the detection of the shape of the front surface of the bone.

10. A method of diagnosing bone strength, comprising:
  detecting a shape of a front surface of a bone covered with soft tissues;
  transmitting an ultrasonic wave obliquely to the bone, for deriving the speed of sound;
  receiving the ultrasonic wave that exits from the bone to the side of the soft tissues at a plurality of locations, the ultrasonic wave being received after it is transmitted and propagates along the front surface of the bone; and
  deriving a speed of sound of the ultrasonic wave that propagates along the front surface of the bone based on the received wave signal and the detected shape of the front surface of the bone,
  wherein the step of detecting a shape comprises:
    transmitting the ultrasonic wave to the bone,
    receiving a front-surface reflected wave of the ultrasonic wave from the front surface of the bone, the ultrasonic wave being transmitted by the step of transmitting the ultrasonic wave to the bone, and
    detecting the shape of the front surface of the bone using the wave signal received by the step of receiving the front-surface reflected wave,
  wherein the step of transmitting the ultrasonic wave to the bone transmits ultrasonic waves simultaneously, using a plurality of wave-transmission transducers; and
  wherein the step of receiving a front-surface reflected wave receives the front-surface reflected wave, using a plurality of wave-reception transducers; and
  wherein the step of detecting the shape of the front surface of the bone comprises:
    detecting an incoming direction of the front-surface reflected wave using a time difference between times when two wave-reception transducers constituting each transducer group receive the front-surface reflected wave, each transducer group including adjacent two wave-reception transducers among the plurality of wave-reception transducers;
    detecting a propagation time of the front-surface reflected wave that reaches each transducer group using the received wave signal of the front-surface reflected wave of at least one wave-reception transducer among the two wave-reception transducers constituting each transducer group;
    detecting a plurality of reflection points of the ultrasonic wave on the front surface of the bone based on the incoming direction and the propagation time of the front-surface reflected wave detected for each transducer group by the step of detecting the incoming direction and the propagation time detected by said detecting step, respectively; and
    deriving the shape of the front surface of the bone using the plurality of reflection points on the front surface of the bone, the reflection points being detected for the plurality of transducer groups having different transducers by the step of detecting the reflection point of the ultrasonic wave.

* * * * *